US006511665B1

(12) United States Patent
Dower et al.

(10) Patent No.: US 6,511,665 B1
(45) Date of Patent: Jan. 28, 2003

(54) ANTIBODIES TO INTERLEUKIN-1 RECEPTORS

(75) Inventors: Steven K. Dower, Redmond, WA (US); Carl J. March, Winslow, WA (US); John E. Sims, Seattle, WA (US); David L. Urdal, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 08/452,775

(22) Filed: May 30, 1995

Related U.S. Application Data

(63) Continuation of application No. 07/575,911, filed on Aug. 31, 1990, now abandoned, which is a continuation-in-part of application No. 07/258,756, filed on Oct. 13, 1988, now Pat. No. 5,081,228, which is a continuation-in-part of application No. 07/160,550, filed on Feb. 25, 1988, now Pat. No. 4,968,607, which is a continuation-in-part of application No. 07/125,627, filed on Nov. 25, 1987, now abandoned.

(51) Int. Cl.$^7$ ............... A61K 39/395; C07K 16/28; C12N 5/12
(52) U.S. Cl. ................ 424/154.1; 424/130.1; 424/133.1; 424/139.1; 424/141.1; 424/142.1; 424/143.1; 424/144.1; 424/152.1; 424/153.1; 424/173.1; 530/387.1; 530/387.3; 530/387.9; 530/388.1; 530/388.15; 530/388.2; 530/388.22; 530/388.7; 530/388.73; 530/388.75; 435/331; 435/334; 435/343.2; 435/346
(58) Field of Search .................. 424/139.1, 141.1, 424/143.1, 144.1, 152.1, 153.1, 173.1, 154.1; 435/70.21, 172.2, 240.27, 326, 332, 343.1; 530/350, 387.9, 388.1, 388.22, 388.7, 388.73, 389.6, 388.75

(56) References Cited

U.S. PATENT DOCUMENTS

| | | | |
|---|---|---|---|
| 4,411,993 A | * | 10/1983 | Gillis |
| 4,522,918 A | * | 6/1985 | Schlom et al. |
| 4,578,335 A | | 3/1986 | Urdal et al. |
| 4,675,285 A | | 6/1987 | Clark et al. |
| 4,707,443 A | | 11/1987 | Nelson et al. |
| 4,968,607 A | * | 11/1990 | Dower et al. |
| 5,006,459 A | * | 4/1991 | Kung et al. |
| 5,043,281 A | * | 8/1991 | Masuho et al. |
| 5,081,228 A | * | 1/1992 | Dower et al. |

FOREIGN PATENT DOCUMENTS

| | | |
|---|---|---|
| JP | 1053300 | 3/1989 |

OTHER PUBLICATIONS

Muchmore et al. (1985) Science 229:479–481.*
Potocnjak et al. (1982) Science 215:1637–1639.*
Malavarca, R., et al., Program & Abstrcts for the Fifth International Lymphokine Workshop, Jan. 11–15, 1987, Clearwater, Florida, as published in Lymphokine Research, vol. 6, No. 1, Abstract No. 1238 (Winter, 1987).*

Paganelli, K.A., et al., The Journal of Immunology, vol. 138, No. 7, pp. 2249–2253, Apr., 1987.*
Harris et al. TibTech 11: 42–44 (1993).*
D'Narello et al. Blood 77:1627–1652 (1991).*
Steiner et al. BioTechnology 11:644 (1993).*
Rhem BioTechnology Newswatch Oct. 4, 1993 p. 1 (1993).*
Weir Handbook Exper. Immunology 4th ed. 1986 pp. 8.14–8.15.*
All other ref's of record.*
Craig Bioworld Today Jul. 19, 1994 p.1,3.*
Faherty et al. J. Immunol. 148:766–771 (1992).*
Sims et al. PNAS 86:8946–8950 (1989).*
Dower et al. J. Immunol 142:4314–4320 (1989).*
Scopes (1987) Protein Purification–Principles and Practice, 2d ed., Springer–Verlag, N.Y., pp. vii–viii and Table of Contents.*
Sims et al. PNAS 90:6155–6159 (1993) (Cited by Applicant not Provided).*
Lennard Crit. Rev. Immunol. 15(1) 77–105 (1995).*
Rangnekar et al., "Immunoprecipitation of interleukin–1 receptors from a mouse thymoma cell line, EL–4," *J. Biol. Chem.* 263:16408, 1988.
Rangnekar and Plate, Interleukin–1 receptor–like proteins synthesized by translation, in vitro, of immunopurified polysomal messenger RNA, *J. Biol. Chem.* 263:16414, 1988.
Bomsztyk et al., "Evidence for different interleukin–1 receptors in murine B– and T–cell lines," *Proc. Natl. Acad. Sci. USA* 86:8034, 1989.
Chizzonite et al., "Two high–affinity interleukin 1 receptors represent separate gene products," *Proc. Natl. Acad. Sci. USA* 86:8029, 1989.
Dower, et al., "Retention of ligand binding activity by the extracellular domain of the IL–1 receptor," *J. Immunol.* 142:4314,1989.
Gallis et al., "IL–1 induces rapid phosphorylation of the IL–1 receptor," *J. Immunol.* 143:3235, 1989.
Slack et al., "Application of the multiscreen system to cytokine radioreceptor assays," *BioTechniques* 7:1132, 1989.
Curtis et al., "IL–1 and its receptor are translocated to the nucleus," *J. Immunol.* 144:1295, 1990.
Lewis et al., "Monoclonal antibodies reacting with the interleukin 1 receptor define a multi–molecular complex," *Eur. J. Immunol.* 20:207, 1990.
Dower et al., "Similarity between the interleukin 1 receptors on a murine T–lymphoma cell line and on a murine fibroblast cell line," *Proc. Natl. Acad. Sci. USA* 83:1060, 1986.
Kilian et al., "Interleukin 1a and interleukin 1b bind to the same receptor on T cells," *J. Immunol.* 136:4509, 1986.

(List continued on next page.)

*Primary Examiner*—Phillip Gambel
(74) *Attorney, Agent, or Firm*—Janis C. Henry

(57) ABSTRACT

The present invention provides monoclonal antibodies and binding proteins which specifically bind to the IL-1 receptor. Also provided are methods for detecting IL-1 receptors on cells, and for detecting soluble IL-1 receptors in serum.

42 Claims, 14 Drawing Sheets

OTHER PUBLICATIONS

Matsushima et al., "Properties of a specific interleukin 1 receptor on human Epstein Barr virus–transformed . . . " *J. Immunol.* 136:4496, 1986.

Bird et al., "Identifications of a common class of high affinity receptors for both types of porcine interleukin–1 on connective tissue cells," *Nature* 324:263, 1986.

Dower et al., The cell surface receptors for interleukin–1a and interleukin–1b are indentical, *Nature* 324:266, 1986.

Bron and MacDonald, Identification of the plasma membrane receptor for interleukin–1 on mouse thymoma cells, *FEBS Lett.* 219:365, 1987.

Chin et al, "Identification of a high–affinity receptor for native human interleukin 1b and interleukin 1a on normal human lung fibroblasts," *J. Exp. Med.* 165:70, 1987.

Mosley et al., "The interleukin–1 receptor binds to the human interleukin–1a precursor but not the interleukin–1b precursor," *J. Biol. Chem.* 262:2941, 1987.

Paganelli et al., "Detergent solubilization of the interleukin 1 receptor," *J. Immunol.* 138:2249, 1987.

Martin et al., "Interleukin 1 induces specific phophorylation of a 41 kDa plasma membrane protein from the human tumor cell line K 562," *Immunobiol.* 171:165, 1986.

Oppenheim et al., "There is more than one interleukin 1," *Immunol. Today* 7:45, 1986.

Thieme et al., "Recombinant murine and human IL–1a bind to human endothelial cells with an equal affinity, but have an unequal ability to induce endothelial cell adherence of lymphocytes," *J. Immunol.* 139:1173, 1987.

Lowenthal and MacDonald, "Binding and Internalization of Interleukin 1 by T Cells," *J. Exp. Med.* 164:1060, 1986.

Matsushima, et al., "Phosphorylation of a Cytosolic 65–kDa Protein induced by Interleukin 1 in Glucocorticoid Pre–Treated Normal Human Peripheral Blood Mononuclear Leukocytes," *J. Immunol.* 139:3367 (1987).

Suggs et al., "Use of synthetic oligonucleotides as hybridization probes: Isolation of cloned cDNA sequences for human B2–Microglobin," *Proc. Natl. Acad. Sci. USA* 78(11):6613, 1981.

Okayama and Berg, *Molecular and Cellular Biology* 3:280, 1983; "A cDNA cloning vector that permits expression of cDNA inserts in mammaliam cells."

Okayama and Berg, "High–efficiency cloning of full–length cDNA," *Molecular and Cellular Biology* 2:161, 1982.

Dower et al., "Detection and Characterization of High Affinity Plasma Membrane for Human Interleukin–1" *J. Exp. Med.* 162:501, 1985.

Nikaido et al., Molecular cloning of cDNA encoding human interleukin–2 receptor, *Nature* 311:631, 1984.

Shirakawa et al., "Expression of Interleukin 1 Receptors on Human Peripheral T–Cells," *J. Immunol.* 138:4243, 1988.

Parikh et al., "Affinity Chromatography," C&EN, Aug. 26, 1985, p. 17.

Mizel et al.; Preparation of Goat Antibodies Against Interleukin 1: Use of an Immunoadsorbent to Purify Interleukin 1; J. Immunol. 131:1834, 1987.

Newton et al.: Human Recombinant $^{125}$Interleukin–1b: A Stable, High–Affinity Reagent for Analyzing IL–1 Receptors; Biotechnology Update 2:13, 1987.

Hiraki et al., Isolation and characterization of expressible cDNA clones for mouse thy–1: A model system for cDNA expression of cell surface proteins, *J. Immunol.* 136:4291, 1986.

Maniatis et al., "Molecular Cloning: A Laboratory Manual," pp. 225–45, 412–27 (Cold Spring Harbor Laboratory, 1982).

Macdonald et al., "Cell surface glycoproteins involved in the stimulation of interleukin 1–dependent interleukin 2 production by a subline of EL4 thymoma cells," *J. Immunol.* 135:3944, 1985.

Luscher et al., "Cell surface glycoproteins involved in the stimulation of interleukin 1–dependent interleukin 2 production by a subline of EL4 thymoma cells: Structure, Biosynthesis and Maturation," *J. Immunol.* 135:3951 1985.

Kikutani et al., "Molecular Structure of Human Lymphocyte Receptor for Immunoglobulin E," *Cell* 47:657, 1986.

Dower and Urbal, "The interleukin–1 receptor," *Immunology Today* 8:46, 1987.

Dartmann, et al., "The Nucleotide Sequence and Genome Organization of Human Papilloma Virus Type II," *Virology* 151:124, 1986.

Perlman et al., "Putative Signal Peptidase Recognition Site and Sequence in Eukaryotic and Prokaryotic Signal Peptides," *J. Mol. Biol.* 167:391, 1983.

Robinson et al. (Ed.), Introduction to Proteins and Protein Engineering (Elsevier), 1986, p. 258–9.

* cited by examiner

```
   1  5'-TGGGTCGTCT GACTAGAAGT GAGCTGTCTG TCATTCTTGT GCACGCCAGC
  51     CCAGTAATCA TTTGGAGGCA AAGCAAACTG TAAGTAATGC TGTCCTGGGC
 101     TGACTTGAGG AGGCAGTTTT CGTTTTAACA GCCAGTGTTT ATTTGCTCAG
 151     CAAACGTTGT CTCGGGGAGA AATGTCGCTG GATGTCATCA GAGTTCCCAG
 201     TGCCCCGAAC CGTGAACAAC ACAAATGGAG AATATGAAAG TGCTACTGGG
 251     GCTCATTTGT CTCATGGTGC CTCTGCTGTC GCTGGAGATT GACGTATGTA
 301     CAGAATATCC AAATCAGATC GTTTTGTTTT TATCTGTAAA TGAAATTGAT
 351     ATTCGCAAGT GTCCTCTTAC TCCAAATAAA ATGCACGGCG ACACCATAAT
 401     TTGGTACAAG AATGACAGCA AGACCCCCAT ATCAGCGGAC CGGGACTCCA
 451     GGATTCATCA GCAGAATGAA CATCTTTGGT TTGTACCTGC CAAGGTGGAG
 501     GACTCAGGAT ATTACTATTG TATAGTAAGA AACTCAACTT ACTGCCTCAA
 551     AACTAAAGTA ACCGTAACTG TGTTAGAGAA TGACCCTGGC TTGTGTTACA
 601     GCACACAGGC CACCTTCCCA CAGCGGCTCC ACATTGCCGG GGATGGAAGT
 651     CTTGTGTGCC CTTATGTGAG TTATTTAAA GATGAAAATA ATGAGTTACC
 701     CGAGGTCCAG TGGTATAAGA ACTGTAAACC TCTGCTTCTT GACAACGTGA
 751     GCTTCTTCGG AGTAAAAGAT AAACTGTTGG TGAGGAATGT GGCTGAAGAG
 801     CACAGAGGGG ACTATATATG CCGTATGTCC TATACGTTCC GGGGGAAGCA
 851     ATATCCGGTC ACACGAGTAA TACAATTTAT CACAATAGAT GAAAACAAGA
 901     GGGACAGACC TGTTATCCTG AGCCCTCGGA ATGAGACGAT CGAAGCTGAC
 951     CCAGGATCAA TGATACAACT GATCTGCAAC GTCACGGGCC AGTTCTCAGA
1001     CCTTGTCTAC TGGAAGTGGA ATGGATCAGA AATTGAATGG AATGATCCAT
1051     TTCTAGCTGA AGACTATCAA TTTGTGGAAC ATCCTTCAAC CAAAAGAAAA
1101     TACACACTCA TTACAACACT TAACATTTCA GAAGTTAAAA GCCAGTTTTA
1151     TCGCTATCCG TTTATCTGTG TTGTTAAGAA CACAAATATT TTTGAGTCGG
1201     CGCATGTGCA GTTAATATAC CCAGTCCCTG ACTTCAAGAA TTACCTCATC
1251     GGGGGCTTTA TCATCCTCAC GGCTACAATT GTATGCTGTG TGTGCATCTA
1301     TAAAGTCTTC AAGGTTGACA TAGTGCTTTG GTACAGGGAC TCCTGCTCTG
1351     GTTTTCTTCC TTCAAAAGCT TCAGATGGAA AGACATACGA TGCCTATATT
1401     CTTTATCCCA AGACCCTGGG AGAGGGGTCC TTCTCAGACT TAGATACTTT
1451     TGTTTTTAAA CTGTTGCCTG AGGTCTTGGA GGGACAGTTT GGATACAAGC
1501     TGTTCATTTA TGGAAGGGAT GACTATGTTG GAGAAGATAC CATCGAGGTT
1551     ACTAATGAAA ATGTAAAGAA AAGCAGGAGG CTGATTATCA TTCTAGTGAG
1601     AGATATGGGA GGCTTCAGCT GGCTGGGCCA GTCATCTGAA GAGCAAATAG
1651     CCATATACAA TGCTCTCATC CAGGAAGGAA TTAAAATCGT CCTGCTTGAG
1701     TTGGAGAAAA TCCAAGACTA TGAGAAAATG CCAGATTCTA TTCAGTTCAT
1751     TAAGCAGAAA CACGGAGTCA TTTGCTGGTC AGGAGACTTT CAAGAAAGAC
1801     CACAGTCTGC AAAGACCAGG TTCTGGAAAA ACTTAAGATA CCAGATGCCA
1851     GCCCAACGGA GATCACCATT GTCTAAACAC CGCTTACTAA CCCTGGATCC
1901     TGTGCGGGAC ACTAAGGAGA AACTGCCGGC AGCAACACAC TTACCACTCG
1951     GCTAGCATGG CAAAAGTGGG CAGGCCAAGA ACTTCGGAAT ATCTCCCATC
2001     ATAAGAGGCT GCAGCTGGGC TGTGCCTCCC AGTAAAACAG TCACGAACCA
2051     AACCTGTGCA GTCCCTTGTT CCAGATCACC TGGAACTGGA TTGGGAAGAG
2101     AACAGGACTT GGTGGCCAGG ACCGCTCAGA GAGCCATGGT TGCTCAGGGA
2151     TGCTGCTCCG GGATGCTTGA CTAACAGTCG AGGCAGTGAA CTGGGTGTAG
2201     AAAGCGTCAG GAAATGGCCA CATGTGTGGA TGGTTTAATT AGATTCTGTG
2251     GAGTCTCACA GTGGGATTGT GGCTGTCTGA GGACACTTTG GGGGTCGCT
2301     GTCCAAGAAG TGGCTCCCCA AGTATAAGT GCGGGTGAGG TTTACTGATA
2351     CCCCAC-3'
```

*Figure 2*

```
5'-ATG GAG AAT ATG AAA GTG CTA CTG GGG CTC ATT TGT CTC ATG GTG      -15
   Met Glu Asn Met Lys Val Leu Leu Gly Leu Ile Cys Leu Met Val       -5

CCT CTG CTG TCG CTG GAG ATT GAC GTA TGT ACA GAA TAT CCA AAT       33
   Pro Leu Leu Ser Leu Glu Ile Asp Val Cys Thr Glu Tyr Pro Asn       11

CAG ATC GTT TTG TTT TTA TCT GTA AAT GAA ATT GAT ATT CGC AAG       78
   Gln Ile Val Leu Phe Leu Ser Val Asn Glu Ile Asp Ile Arg Lys       26

TGT CCT CTT ACT CCA AAT AAA ATG CAC GGC GAC ACC ATA ATT TGG       123
   Cys Pro Leu Thr Pro Asn Lys Met His Gly Asp Thr Ile Ile Trp       41

TAC AAG AAT GAC AGC AAG ACC CCC ATA TCA GCG GAC CGG GAC TCC       168
   Tyr Lys Asn Asp Ser Lys Thr Pro Ile Ser Ala Asp Arg Asp Ser       56

AGG ATT CAT CAG CAG AAT GAA CAT CTT TGG TTT GTA CCT GCC AAG       213
   Arg Ile His Gln Gln Asn Glu His Leu Trp Phe Val Pro Ala Lys       71

GTG GAG GAC TCA GGA TAT TAC TAT TGT ATA GTA AGA AAC TCA ACT       258
   Val Glu Asp Ser Gly Tyr Tyr Tyr Cys Ile Val Arg Asn Ser Thr       86

TAC TGC CTC AAA ACT AAA GTA ACC GTA ACT GTG TTA GAG AAT GAC       303
   Tyr Cys Leu Lys Thr Lys Val Thr Val Thr Val Leu Glu Asn Asp       101

CCT GGC TTG TGT TAC AGC ACA CAG GCC ACC TTC CCA CAG CGG CTC       348
   Pro Gly Leu Cys Tyr Ser Thr Gln Ala Thr Phe Pro Gln Arg Leu       116

CAC ATT GCC GGG GAT GGA AGT CTT GTG TGC CCT TAT GTG AGT TAT       393
   His Ile Ala Gly Asp Gly Ser Leu Val Cys Pro Tyr Val Ser Tyr       131

TTT AAA GAT GAA AAT AAT GAG TTA CCC GAG GTC CAG TGG TAT AAG       438
   Phe Lys Asp Glu Asn Asn Glu Leu Pro Glu Val Gln Trp Tyr Lys       146

AAC TGT AAA CCT CTG CTT CTT GAC AAC GTG AGC TTC TTC GGA GTA       483
   Asn Cys Lys Pro Leu Leu Leu Asp Asn Val Ser Phe Phe Gly Val       161

AAA GAT AAA CTG TTG GTG AGG AAT GTG GCT GAA GAG CAC AGA GGG       528
   Lys Asp Lys Leu Leu Val Arg Asn Val Ala Glu Glu His Arg Gly       176

GAC TAT ATA TGC CGT ATG TCC TAT ACG TTC CGG GGG AAG CAA TAT       573
   Asp Tyr Ile Cys Arg Met Ser Tyr Thr Phe Arg Gly Lys Gln Tyr       191

CCG GTC ACA CGA GTA ATA CAA TTT ATC ACA ATA GAT GAA AAC AAG       618
   Pro Val Thr Arg Val Ile Gln Phe Ile Thr Ile Asp Glu Asn Lys       206
```

*Figure 3A*

```
AGG GAC AGA CCT GTT ATC CTG AGC CCT CGG AAT GAG ACG ATC GAA      663
Arg Asp Arg Pro Val Ile Leu Ser Pro Arg Asn Glu Thr Ile Glu      221

GCT GAC CCA GGA TCA ATG ATA CAA CTG ATC TGC AAC GTC ACG GGC      708
Ala Asp Pro Gly Ser Met Ile Gln Leu Ile Cys Asn Val Thr Gly      236

CAG TTC TCA GAC CTT GTC TAC TGG AAG TGG AAT GGA TCA GAA ATT      753
Gln Phe Ser Asp Leu Val Tyr Trp Lys Trp Asn Gly Ser Glu Ile      251

GAA TGG AAT GAT CCA TTT CTA GCT GAA GAC TAT CAA TTT GTG GAA      798
Glu Trp Asn Asp Pro Phe Leu Ala Glu Asp Tyr Gln Phe Val Glu      266

CAT CCT TCA ACC AAA AGA AAA TAC ACA CTC ATT ACA ACA CTT AAC      843
His Pro Ser Thr Lys Arg Lys Tyr Thr Leu Ile Thr Thr Leu Asn      281

ATT TCA GAA GTT AAA AGC CAG TTT TAT CGC TAT CCG TTT ATC TGT      888
Ile Ser Glu Val Lys Ser Gln Phe Tyr Arg Tyr Pro Phe Ile Cys      296

GTT GTT AAG AAC ACA AAT ATT TTT GAG TCG GCG CAT GTG CAG TTA      933
Val Val Lys Asn Thr Asn Ile Phe Glu Ser Ala His Val Gln Leu      311

ATA TAC CCA GTC CCT GAC TTC AAG AAT TAC CTC ATC GGG GGC TTT      978
Ile Tyr Pro Val Pro Asp Phe Lys Asn Tyr Leu Ile Gly Gly Phe      326

ATC ATC CTC ACG GCT ACA ATT GTA TGC TGT GTG TGC ATC TAT AAA     1023
Ile Ile Leu Thr Ala Thr Ile Val Cys Cys Val Cys Ile Tyr Lys      341

GTC TTC AAG GTT GAC ATA GTG CTT TGG TAC AGG GAC TCC TGC TCT     1068
Val Phe Lys Val Asp Ile Val Leu Trp Tyr Arg Asp Ser Cys Ser      356

GGT TTT CTT CCT TCA AAA GCT TCA GAT GGA AAG ACA TAC GAT GCC     1113
Gly Phe Leu Pro Ser Lys Ala Ser Asp Gly Lys Thr Tyr Asp Ala      371

TAT ATT CTT TAT CCC AAG ACC CTG GGA GAG GGG TCC TTC TCA GAC     1158
Tyr Ile Leu Tyr Pro Lys Thr Leu Gly Glu Gly Ser Phe Ser Asp      386

TTA GAT ACT TTT GTT TTT AAA CTG TTG CCT GAG GTC TTG GAG GGA     1203
Leu Asp Thr Phe Val Phe Lys Leu Leu Pro Glu Val Leu Glu Gly      401

CAG TTT GGA TAC AAG CTG TTC ATT TAT GGA AGG GAT GAC TAT GTT     1248
Gln Phe Gly Tyr Lys Leu Phe Ile Tyr Gly Arg Asp Asp Tyr Val      416

GGA GAA GAT ACC ATC GAG GTT ACT AAT GAA AAT GTA AAG AAA AGC     1293
Gly Glu Asp Thr Ile Glu Val Thr Asn Glu Asn Val Lys Lys Ser      431
```

*Figure 3B*

```
AGG AGG CTG ATT ATC ATT CTA GTG AGA GAT ATG GGA GGC TTC AGC    1338
Arg Arg Leu Ile Ile Ile Leu Val Arg Asp Met Gly Gly Phe Ser     446

TGG CTG GGC CAG TCA TCT GAA GAG CAA ATA GCC ATA TAC AAT GCT    1383
Trp Leu Gly Gln Ser Ser Glu Glu Gln Ile Ala Ile Tyr Asn Ala     461

CTC ATC CAG GAA GGA ATT AAA ATC GTC CTG CTT GAG TTG GAG AAA    1428
Leu Ile Gln Glu Gly Ile Lys Ile Val Leu Leu Glu Leu Glu Lys     476

ATC CAA GAC TAT GAG AAA ATG CCA GAT TCT ATT CAG TTC ATT AAG    1473
Ile Gln Asp Tyr Glu Lys Met Pro Asp Ser Ile Gln Phe Ile Lys     491

CAG AAA CAC GGA GTC ATT TGC TGG TCA GGA GAC TTT CAA GAA AGA    1518
Gln Lys His Gly Val Ile Cys Trp Ser Gly Asp Phe Gln Glu Arg     506

CCA CAG TCT GCA AAG ACC AGG TTC TGG AAA AAC TTA AGA TAC CAG    1563
Pro Gln Ser Ala Lys Thr Arg Phe Trp Lys Asn Leu Arg Tyr Gln     521

ATG CCA GCC CAA CGG AGA TCA CCA TTG TCT AAA CAC CGC TTA CTA    1608
Met Pro Ala Gln Arg Arg Ser Pro Leu Ser Lys His Arg Leu Leu     536

ACC CTG GAT CCT GTG CGG GAC ACT AAG GAG AAA CTG CCG GCA GCA    1653
Thr Leu Asp Pro Val Arg Asp Thr Lys Glu Lys Leu Pro Ala Ala     551

ACA CAC TTA CCA CTC GGC TAG-3'                                  1671
Thr His Leu Pro Leu Gly End                                      557
```

*Figure 3C*

```
   1 5'-AGACGCACCC TCTGAAGATG GTGGACTCCC TCCTGAGAAG CTGGGACCCC
  51    TTGGTAAAAG ACAAGGCCTT CTCCAAGAAG AATATGAAAG TGTTACTCAG
 101    ACTTATTTGT TTCATAGCTC TACTGATTTC TTCTCTGGAG GCTGATAAAT
 151    GCAAGGAACG TGAAGAAAAA ATAATTTTAG TGTCATCTGC AAATGAAATT
 201    GATGTTCGTC CCTGTCCTCT TAACCCAAAT GAACACAAAG GCACTATAAC
 251    TTGGTATAAA GATGACAGCA AGACACCTGT ATCTACAGAA CAAGCCTCCA
 301    GGATTCATCA ACACAAAGAG AAACTTTGGT TTGTTCCTGC TAAGGTGGAG
 351    GATTCAGGAC ATTACTATTG CGTGGTAAGA AATTCATCTT ACTGCCTCAG
 401    AATTAAAATA AGTGCAAAAT TTGTGGAGAA TGAGCCTAAC TTATGTTATA
 451    ATGCACAAGC CATATTTAAG CAGAAACTAC CCGTTGCAGG AGACGGAGGA
 501    CTTGTGTGCC CTTATATGGA GTTTTTTAAA AATGAAAATA ATGAGTTACC
 551    TAAATTACAG TGGTATAAGG ATTGCAAACC TCTACTTCTT GACAATATAC
 601    ACTTTAGTGG AGTCAAAGAT AGGCTCATCG TGATGAATGT GGCTGAAAAG
 651    CATAGAGGGA ACTATACTTG TCATGCATCC TACACATACT TGGGCAAGCA
 701    ATATCCTATT ACCCGGGTAA TAGAATTTAT TACTCTAGAG GAAAACAAAC
 751    CCACAAGGCC TGTGATTGTG AGCCCAGCTA ATGAGACAAT GGAAGTAGAC
 801    TTGGGATCCC AGATACAATT GATCTGTAAT GTCACCGGCC AGTTGAGTGA
 851    CATTGCTTAC TGGAAGTGGA ATGGGTCAGT AATTGATGAA GATGACCCAG
 901    TGCTAGGGGA AGACTATTAC AGTGTGGAAA ATCCTGCAAA CAAAAGAAGG
 951    AGTACCCTCA TCACAGTGCT TAATATATCG GAAATTGAAA GTAGATTTTA
1001    TAAACATCCA TTTACCTGTT TTGCCAAGAA TACACATGGT ATAGATGCAG
1051    CATATATCCA GTTAATATAT CCAGTCACTA ATTCCAGAA GCACATGATT
1101    GGTATATGTG TCACGTTGAC AGTCATAATT GTGTGTTCTG TTTTCATCTA
1151    TAAAATCTTC AAGATTGACA TTGTGCTTTG GTACAGGGAT TCCTGCTATG
1201    ATTTTCTCCC AATAAAAGCT TCAGATGGAA AGACCTATGA CGCATATATA
1251    CTGTATCCAA AGACTGTTGG GGAAGGGTCT ACCTCTGACT GTGATATTTT
1301    TGTGTTTAAA GTCTTGCCTG AGGTCTTGGA AAAACAGTGT GGATATAAGC
1351    TGTTCATTTA TGGAAGGGAT GACTACGTTG GGGAAGACAT TGTTGAGGTC
1401    ATTAATGAAA ACGTAAAGAA AAGCAGAAGA CTGATTATCA TTTTAGTCAG
1451    AGAAACATCA GGCTTCAGCT GGCTGGGTGG TTCATCTGAA GAGCAAATAG
1501    CCATGTATAA TGCTCTTGTT CAGGATGGAA TTAAAGTTGT CCTGCTTGAG
1551    CTGGAGAAAA TCCAAGACTA TGAGAAAATG CCAGAATCGA TTAAATTCAT
1601    TAAGCAGAAA CATGGGGCTA TCCGCTGGTC AGGGGACTTT ACACAGGGAC
1651    CACAGTCTGC AAAGACAAGG TTCTGGAAGA ATGTCAGGTA CCACATGCCA
1701    GTCCAGCGAC GGTCACCTTC ATCTAAACAC CAGTTACTGT CACCAGCCAC
1751    TAAGGAGAAA CTGCAAAGAG AGGCTCACGT GCCTCTCGGG TAGCATGGAG
1801    AAGTTGCCAA GAGTTCTTTA GGTGCCTCCT GTCTTATGGC GTTGCAGGCC
1851    AGGTTATGCC TCATGCTGAC TTGCAGAGTT CATGGAATGT AACTATATCA
1901    TCCTTTATCC CTGAGGTCAC CTGGAATCAG ATTATTAAGG GAATAAGCCA
1951    TGACGTCAAT AGCAGCCCAG GGCACTTCAG AGTAGAGGGC TTGGGAAGAT
2001    CTTTTAAAAA GGCAGTAGGC CCGGTGTGGT GGCTCACGCC TATAATCCCA
2051    GCACTTTGGG AGGCTGAAGT GGGTGGATCA CCAGAGGTCA GGAGTTCGAG
2101    ACCAGCCCAG CCAACATGGC AAAACCCCAT CTCTACTAAA AATACAAAAA
2151    TGAGCTAGGC ATGGTGGCAC ACGCCTGTAA TCCCAGCTAC ACCTGAGGCT
2201    GAGGCAGGAG AATTGCTTGA ACCGGGGAGA CGGAGGTTGC AGTGAGCCGA
2301    GTTTGGGCCA CTGCACTCTA GCCTGGCAAC AGAGCAAGAC TCCGTCTCAA
2351    AAAAAGGGCA ATAAATGCCC TCTCTGAATG TTTGAACTGC AAGAAAAGG
2401    CATGGAGACA GCGAACTAGA AGAAAGGGCA AGAAGGAAAT AGCCACCGTC
2451    TACAGATGGC TTAGTTAAGT CATCCACAGC CCAAGGGCGG CGGCTATGCC
2501    TTGTCTGGGG ACCCTGTAGA GTCACTGACC CTGGAGCGGC TCTCCTGAGA
2551    GGTGCTGCAG GCAAAGTGAG ACTGACACCT CACTGAGGAA GGGAGACATA
2601    TTCTTGGAGA ACTTTCCATC TGCTTGTATT TTCCATACAC ATCCCCAGCC-3'
```

*Figure 4*

```
ATG AAA GTG TTA CTC AGA CTT ATT TGT TTC ATA GCT CTA CTG ATT      -9
Met Lys Val Leu Leu Arg Leu Ile Cys Phe Ile Ala Leu Leu Ile      -3

TCT TCT CTG GAG GCT GAT AAA TGC AAG GAA CGT GAA GAA AAA ATA      39
Ser Ser Leu Glu Ala Asp Lys Cys Lys Glu Arg Glu Glu Lys Ile      13

ATT TTA GTG TCA TCT GCA AAT GAA ATT GAT GTT CGT CCC TGT CCT      84
Ile Leu Val Ser Ser Ala Asn Glu Ile Asp Val Arg Pro Cys Pro      28

CTT AAC CCA AAT GAA CAC AAA GGC ACT ATA ACT TGG TAT AAA GAT      129
Leu Asn Pro Asn Glu His Lys Gly Thr Ile Thr Trp Tyr Lys Asp      43

GAC AGC AAG ACA CCT GTA TCT ACA GAA CAA GCC TCC AGG ATT CAT      174
Asp Ser Lys Thr Pro Val Ser Thr Glu Gln Ala Ser Arg Ile His      58

CAA CAC AAA GAG AAA CTT TGG TTT GTT CCT GCT AAG GTG GAG GAT      219
Gln His Lys Glu Lys Leu Trp Phe Val Pro Ala Lys Val Glu Asp      73

TCA GGA CAT TAC TAT TGC GTG GTA AGA AAT TCA TCT TAC TGC CTC      264
Ser Gly His Tyr Tyr Cys Val Val Arg Asn Ser Ser Tyr Cys Leu      88

AGA ATT AAA ATA AGT GCA AAA TTT GTG GAG AAT GAG CCT AAC TTA      309
Arg Ile Lys Ile Ser Ala Lys Phe Val Glu Asn Glu Pro Asn Leu      103

TGT TAT AAT GCA CAA GCC ATA TTT AAG CAG AAA CTA CCC GTT GCA      354
Cys Tyr Asn Ala Gln Ala Ile Phe Lys Gln Lys Leu Pro Val Ala      118

GGA GAC GGA GGA CTT GTG TGC CCT TAT ATG GAG TTT TTT AAA AAT      399
Gly Asp Gly Gly Leu Val Cys Pro Tyr Met Glu Phe Phe Lys Asn      133

GAA AAT AAT GAG TTA CCT AAA TTA CAG TGG TAT AAG GAT TGC AAA      444
Glu Asn Asn Glu Leu Pro Lys Leu Gln Trp Tyr Lys Asp Cys Lys      148

CCT CTA CTT CTT GAC AAT ATA CAC TTT AGT GGA GTC AAA GAT AGG      489
Pro Leu Leu Leu Asp Asn Ile His Phe Ser Gly Val Lys Asp Arg      163

CTC ATC GTG ATG AAT GTG GCT GAA AAG CAT AGA GGG AAC TAT ACT      534
Leu Ile Val Met Asn Val Ala Glu Lys His Arg Gly Asn Tyr Thr      178

TGT CAT GCA TCC TAC ACA TAC TTG GGC AAG CAA TAT CCT ATT ACC      579
Cys His Ala Ser Tyr Thr Tyr Leu Gly Lys Gln Tyr Pro Ile Thr      193

CGG GTA ATA GAA TTT ATT ACT CTA GAG GAA AAC AAA CCC ACA AGG      624
Arg Val Ile Glu Phe Ile Thr Leu Glu Glu Asn Lys Pro Thr Arg      208

CCT GTG ATT GTG AGC CCA GCT AAT GAG ACA ATG GAA GTA GAC TTG      669
Pro Val Ile Val Ser Pro Ala Asn Glu Thr Met Glu Val Asp Leu      223
```

*Figure 5A*

```
GGA TCC CAG ATA CAA TTG ATC TGT AAT GTC ACC GGC CAG TTG AGT     714
Gly Ser Gln Ile Gln Leu Ile Cys Asn Val Thr Gly Gln Leu Ser     238

GAC ATT GCT TAC TGG AAG TGG AAT GGG TCA GTA ATT GAT GAA GAT     759
Asp Ile Ala Tyr Trp Lys Trp Asn Gly Ser Val Ile Asp Glu Asp     253

GAC CCA GTG CTA GGG GAA GAC TAT TAC AGT GTG GAA AAT CCT GCA     804
Asp Pro Val Leu Gly Glu Asp Tyr Tyr Ser Val Glu Asn Pro Ala     268

AAC AAA AGA AGG AGT ACC CTC ATC ACA GTG CTT AAT ATA TCG GAA     849
Asn Lys Arg Arg Ser Thr Leu Ile Thr Val Leu Asn Ile Ser Glu     283

ATT GAA AGT AGA TTT TAT AAA CAT CCA TTT ACC TGT TTT GCC AAG     894
Ile Glu Ser Arg Phe Tyr Lys His Pro Phe Thr Cys Phe Ala Lys     298

AAT ACA CAT GGT ATA GAT GCA GCA TAT ATC CAG TTA ATA TAT CCA     939
Asn Thr His Gly Ile Asp Ala Ala Tyr Ile Gln Leu Ile Tyr Pro     313

GTC ACT AAT TTC CAG AAG CAC ATG ATT GGT ATA TGT GTC ACG TTG     984
Val Thr Asn Phe Gln Lys His Met Ile Gly Ile Cys Val Thr Leu     328

ACA GTC ATA ATT GTG TGT TCT GTT TTC ATC TAT AAA ATC TTC AAG    1029
Thr Val Ile Ile Val Cys Ser Val Phe Ile Tyr Lys Ile Phe Lys     343

ATT GAC ATT GTG CTT TGG TAC AGG GAT TCC TGC TAT GAT TTT CTC    1074
Ile Asp Ile Val Leu Trp Tyr Arg Asp Ser Cys Tyr Asp Phe Leu     358

CCA ATA AAA GCT TCA GAT GGA AAG ACC TAT GAC GCA TAT ATA CTG    1119
Pro Ile Lys Ala Ser Asp Gly Lys Thr Tyr Asp Ala Tyr Ile Leu     373

TAT CCA AAG ACT GTT GGG GAA GGG TCT ACC TCT GAC TGT GAT ATT    1164
Tyr Pro Lys Thr Val Gly Glu Gly Ser Thr Ser Asp Cys Asp Ile     388

TTT GTG TTT AAA GTC TTG CCT GAG GTC TTG GAA AAA CAG TGT GGA    1209
Phe Val Phe Lys Val Leu Pro Glu Val Leu Glu Lys Gln Cys Gly     403

TAT AAG CTG TTC ATT TAT GGA AGG GAT GAC TAC GTT GGG GAA GAC    1254
Tyr Lys Leu Phe Ile Tyr Gly Arg Asp Asp Tyr Val Gly Glu Asp     418

ATT GTT GAG GTC ATT AAT GAA AAC GTA AAG AAA AGC AGA AGA CTG    1299
Ile Val Glu Val Ile Asn Glu Asn Val Lys Lys Ser Arg Arg Leu     433

ATT ATC ATT TTA GTC AGA GAA ACA TCA GGC TTC AGC TGG CTG GGT    1344
Ile Ile Ile Leu Val Arg Glu Thr Ser Gly Phe Ser Trp Leu Gly     448

GGT TCA TCT GAA GAG CAA ATA GCC ATG TAT AAT GCT CTT GTT CAG    1389
Gly Ser Ser Glu Glu Gln Ile Ala Met Tyr Asn Ala Leu Val Gln     463

GAT GGA ATT AAA GTT GTC CTG CTT GAG CTG GAG AAA ATC CAA GAC    1434
Asp Gly Ile Lys Val Val Leu Leu Glu Leu Glu Lys Ile Gln Asp     478
```

*Figure 5B*

```
TAT GAG AAA ATG CCA GAA TCG ATT AAA TTC ATT AAG CAG AAA CAT    1479
Tyr Glu Lys Met Pro Glu Ser Ile Lys Phe Ile Lys Gln Lys His     493

GGG GCT ATC CGC TGG TCA GGG GAC TTT ACA CAG GGA CCA CAG TCT    1524
Gly Ala Ile Arg Trp Ser Gly Asp Phe Thr Gln Gly Pro Gln Ser     508

GCA AAG ACA AGG TTC TGG AAG AAT GTC AGG TAC CAC ATG CCA GTC    1569
Ala Lys Thr Arg Phe Trp Lys Asn Val Arg Tyr His Met Pro Val     523

CAG CGA CGG TCA CCT TCA TCT AAA CAC CAG TTA CTG TCA CCA GCC    1614
Gln Arg Arg Ser Pro Ser Ser Lys His Gln Leu Leu Ser Pro Ala     538

ACT AAG GAG AAA CTG CAA AGA GAG GCT CAC GTG CCT CTC GGG TAG    1656
Thr Lys Glu Lys Leu Gln Arg Glu Ala His Val Pro Leu Gly End     552
```

*Figure 5C* h  MKVLLRLICFIA-LLISSLEADKCKEREEKIILVSSANEIDVRPCPLNPNE-HKG-TITWYKDDSKTPVSTEQASRIHQHKEKLWFVPAK
m  MKVLLGLICLWPLL--SLEIDVCTEYPNQIVLFLSVNEIDIRKCPLTPNKMH-GDTIIWYKNDSKTPISADRDSRIHQQNEHLWFVPAK h  VEDSGHYYCVVRNSSYCLRIKISAKFVENEPNLCYNAQAIPKQKLPVAGDGGLVCPYMEFFKNENNELPKLQWYKDCKPLLLDNIHFSGV
m  VEDSGYYYCIVRNSTYCLKTKVTVTVLENDPGLCYSTQATFPQRLHIAGDGSLVCPVVSYFKDENNELPEVQWYKNCKPLLLDNVSFFGV h  KDRLIVMNVAEKHRGNYTCHASYTYLGKQYPITRVIEFITLEENKPTRPVIVSPANETMEVDLGSQIQLICNVTGQLSDIAYWKWNGSVI
m  KDKLLVRNVAEEHRGDYICRMSYTFRGKQYPVTRVIQFITIDENKRDRPVILSPRNETIEADPGSMIQLICNVTGQFSDLVYWKWNGSEI h  DEDDPVLGEDYYSVENPANKRRSTLITVLNISEIESRFYKHPFTCFAKNTHGIDAAYIQLIYPVTNFQKHMIGICVTLTVIIVCSVFIYK
m  EWNDPFLAEDYQFVEHPSTKRKYTLITTLNISEVKSQFYRYPFICVVKNTNIFESAHVQLIYPVPDFKNYLIGGFIILTATIVCCVCIYK h  IFKIDIVLWYRDSCYDFLPIKASDGKTYDAYILYPKTVGEGSTSDCDIFVFKVLPEVLEKQCGYKLFIYGRDDYVGEDIVEVINENVKKS
m  VFKVDIVLWYRDSCSGFLPSKASDGKTYDAYILYPKTLGEGSFSDLDTFVFKLLPEVLEGQFGYKLFIYGRDDYVGEDTIEVTNENVKKS h  RRLIIILVRETSGFSWLGGSSEEQIAMYNALVQDGIKVVLLELEKIQDYEKMPESIKFIKQKH----------AKTRFWKNVRYH
m  RRLIIILVRDMGGFSWLGQSSEEQIAIYNALIQEGIKIVLLELEKIQDYEKMPDSIQFIKQKHGVICWSGDFQERPQSAKTRFWKNLRYQ h  MPVQRRSPSSKHQLLSPA----TKEKLQREAHVPLG
m  MPAQRRSPLSKHRLLTLDPVRDTKEKLPAATHLPLG

*Figure 8*

ANTIBODIES TO INTERLEUKIN-1 RECEPTORS

CROSS-REFERENCE TO RELATED APPLICATION

This is a filed wrapper continuation of application Ser. No. 07/575,911 filed Aug. 31, 1990, now abandoned, is a continuation-in-part of U.S. application Ser. No. 07/258, 756, filed Oct. 13, 1988, U.S. Pat. No. 5,081,228, which is a continuation-in part of U.S. application Ser. No. 07/160, 550, filed Feb. 25, 1988, U.S. Pat. No. 4,968,607, which is a continuation-in-part of U.S. application Ser. No. 07/125, 627, filed Nov. 25, 1987, abandoned.

TECHNICAL FIELD

The present invention relates generally to antibodies and, more specifically, to antibodies against interleukin-1 receptors.

BACKGROUND OF THE INVENTION

Interleukin-1α and Interleukin-1β (IL-1α and IL-1β) are distantly related polypeptide hormones which play a central role in the regulation of immune and inflammatory responses. These two proteins were originally both classified as IL-1, based on a shared lymphocyte activation factor (LAF) activity, and a common major cellular source, activated macrophages. As information has accumulated from studies using purified natural and recombinant IL-1 molecules, it has become clear that IL-1α and IL-1β each mediate most, if not all, of the wide range of activities previously ascribed to IL-1. The basis for this nearly identical spectrum of biological activities is thought to be a single class of plasma membrane IL-1 receptors which bind both IL-1α and IL-1β. The binding of IL-1 to these receptors is specific, and occurs with a high affinity ($1 \times 10^{-10}$M).

Polyclonal antibodies have long been utilized for various aspects of research and development, but in 1975 Köhler and Milstein discovered a new technique which revolutionized the production and use of antibodies (see Köhler and Milstein, *Nature* 256:495 1975). This technique utilized somatic cell hybridization to generate a continuous "hybridoma" cell line which produced large quantities of a single specific antibody, also referred to as a monoclonal antibody.

It would be beneficial if such antibodies against the IL-1 receptor were available, as they may be useful for diagnosis and therapy, as well as for various research applications. For example, antibodies may be utilized in clinical applications to diagnose the presence of IL-1 receptor in a patient's serum, or may be administered therapeutically to bind to and target IL-1 receptor bearing cells for elimination or neutralization. Additionally, antibodies may be utilized in various research applications such as the purification of recombinantly produced IL-1 receptor, or in assays which detect the presence of the IL-1 receptor.

The present invention provides such antibodies and, furthermore, provides other related advantages.

SUMMARY OF THE INVENTION

The present invention provides monoclonal antibodies which specifically bind to mammalian IL-1 receptors. Within one embodiment of the invention, the monoclonal antibody is selected from the group consisting of human and mouse monoclonal antibodies. Within selected embodiments, the monoclonal antibody blocks the binding of IL-1 to the IL-1 receptor. Within another embodiment the mammalian IL-1 receptor is selected from the group consisting of murine and human IL-1 receptor. Within a related aspect, a therapeutic composition is provided comprising a monoclonal antibody to the IL-1 receptor as described above and a physiologically acceptable carrier or diluent.

Within another aspect of the present invention, a binding protein is provided which specifically binds to a mammalian IL-1 receptor, which may be, for example, a fragment of an antibody or a fusion protein comprising at least one domain derived from an antibody. Within a related aspect, a therapeutic composition is provided comprising a binding protein which specifically binds to mammalian IL-1 receptor, and a physiologically acceptable carrier or diluent.

Within yet another aspect of the present invention, a method for detecting IL-1 receptors on cells is provided comprising the steps of (a) incubating the cells with a monoclonal antibody, as described above, which is labeled, and (b) detecting the presence of bound antibody. Within another aspect, a method for detecting soluble IL-1 receptor in serum is provided comprising the steps of (a) incubating serum suspected of containing soluble IL-1 receptor with a solid support having monoclonal antibodies as described above affixed thereto under conditions and for a time sufficient for binding to occur, (b) incubating the solid support with a second labeled monoclonal antibody specific for mammalian IL-1 receptors under conditions and for a time sufficient for binding to occur, and (c) detecting the presence of bound labeled antibody.

These and other aspects of the present invention will become evident upon reference to the following detailed description and attached drawings.

BRIEF DESCRIPTION OF THE DRAWINGS

FIG. 2 depicts the cDNA sequence of clone GEMBL78. Nucleotides are numbered from the beginning of the fragment. The CTG codon specifying the leucine residue constituting the N-terminus is underlined at position 282, and the TAG terminator codon which ends the open reading frame is underlined at position 1953.

FIGS. 3A–3C depict the cDNA sequence and derived amino acid sequence of the coding region of the cDNA shown in FIG. 2. In FIGS. 3A–3C, nucleotides and amino acids are numbered from the leucine residue representing the N-terminus of the mature protein. In FIGS. 3A–3C, the alternative initiator methionines, N-terminus, and 21 amino acid putative transmembrane region of the murine IL-1 receptor are underlined.

FIG. 4 depicts a cDNA sequence which includes the complete coding region of the human IL-1R gene. Nucleotides are numbered from the beginning of a fragment, designated R3A, which includes the N-terminus and a short sequence of 5' nontranslated DNA. The CTG codon specifying the leucine residue constituting the N-terminus is underlined at position 135, and the TAG terminator codon which ends the open reading frame is underlined at position 1791.

FIGS. 5A–5C depict the cDNA sequence and derived amino acid sequence of the coding region of a cDNA encoding human IL-1 receptor. In FIGS. 5A–5C, nucleotides and amino acids are numbered from the leucine residue (underlined) representing the N-terminus of the mature protein. The 20-amino acid transmembrane region is also underlined.

FIG. 7 provides a graphical comparison of the IL-1 binding characteristics of natural and recombinant IL-1 receptors. In FIG. 7, C indicates the concentration of IL-1 added to the binding incubation (molar); r indicates molecules of IL-1 bound per cell.

FIG. 8 is a comparison of the derived amino acid sequences of the murine and human IL-1 receptors. The transmembrane regions of each protein are underlined, and conserved cysteine residues are indicated by asterisks. Potential N-linked glycosylation sites are indicated by triangles adjacent to asparagine residues.

DETAILED DESCRIPTION OF THE INVENTION

Figure 1:
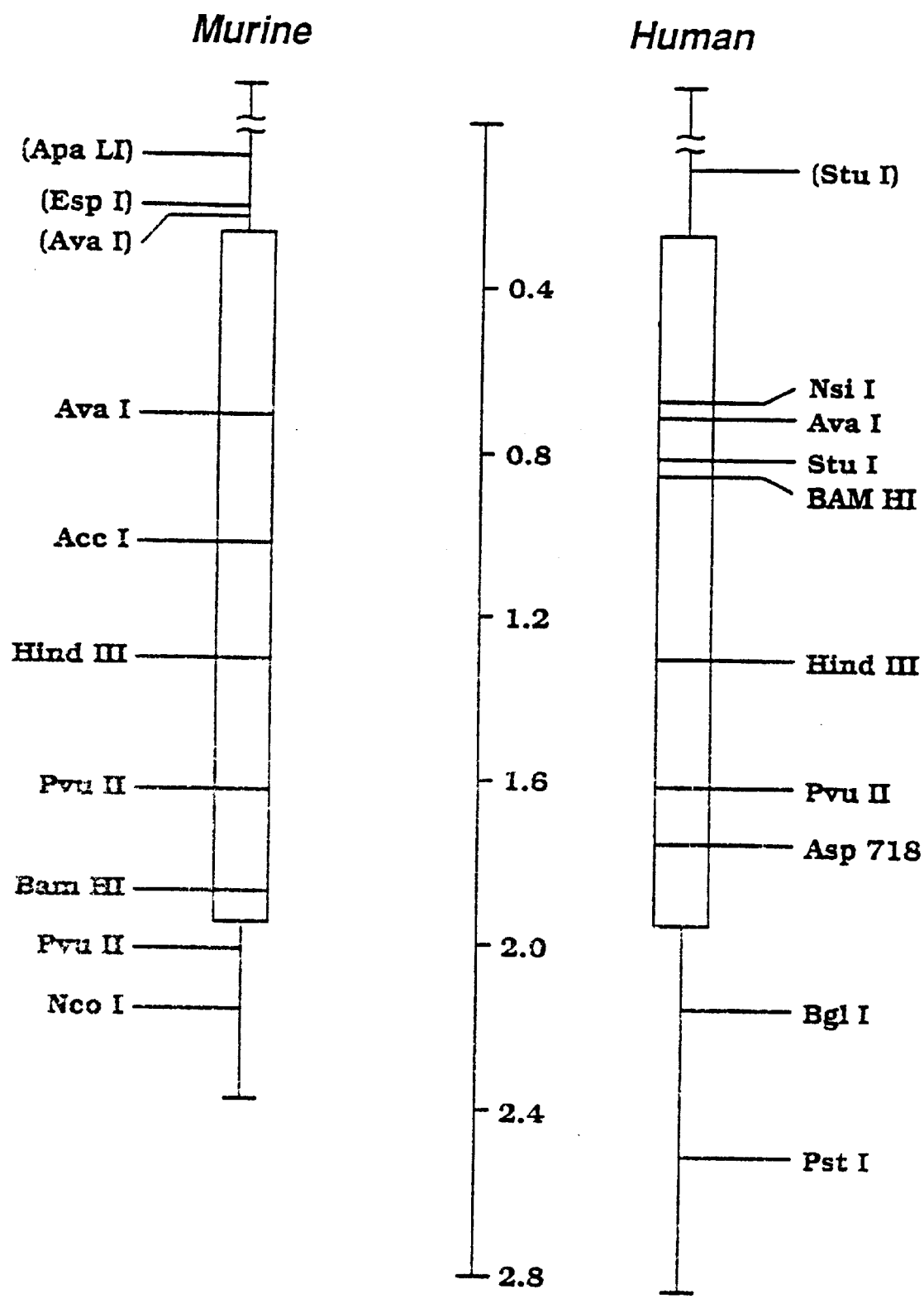
FIG. 1 is a restriction map of cDNA constructs comprising the coding regions of the murine and human IL-1R genes. The murine fragment, isolated from EL-4 6.1 C10 cells and present as an insert in clone GEMBL78, has been deposited with the American Type Culture Collection under deposit accession no. ATCC 67563.

IL-1α and IL-1β apparently regulate the metabolism of cells through a common plasma membrane receptor protein. IL-1 receptor from detergent solutions of EL4 6.1 C10 cells has been stably adsorbed to nitrocellulose with full retention of IL-1 binding activity. This assay system was used to monitor the purification of the IL-1 receptor and to investigate the effects of several chemical modifications on receptor binding activity. IL-1 receptors extracted from EL-4 6.1 C10 cells can be bound to and specifically eluted from IL-1α coupled to Sepharose or other suitable affinity chromatography supports.

Purification by the foregoing process resulted in the identification by silver staining of polyacrylamide gels of a protein of $M_r$ 82,000 daltons that was present in fractions exhibiting IL-1 binding activity. Experiments in which the cell surface proteins of EL-4 cells were radiolabeled and $^{125}$I labeled receptor was purified by affinity chromatography suggested that the $M_r$ 82,000 protein was expressed on the plasma membrane. N-glycanase treatment of this material showed that 21%–35% of the total $M_r$ (82,000) of the receptor was N-lined carbohydrate.

In order to define the chemical properties of the IL-1 receptor, a simple, reproducible and quantitative assay system was devised for the detection of IL-1 receptor in detergent solutions. With this assay, receptor purification can be followed, and changes in receptor binding activity in response to chemical modification of the receptor can be easily monitored.

Binding Assay for IL-1 Receptor

Recombinant human IL-1β and IL-1α can be prepared by expression in *E. coli* and purification to homogeneity as described by Kronheim et al. (*Bio/Technology* 4:1078, 1986). Recombinant human IL-1α is preferably expressed as a polypeptide composed of the C-terminal 157 residues of IL-1α, which corresponds to the $M_r$ 17,500 form of the protein released by activated macrophages. The purified protein is stored at −70° C. in phosphate buffered saline as a stock solution of 3 mg/ml. 10 ∥l (30 μg) aliquots of the stock solution are labeled with sodium ($^{125}$I) iodide by a modified chloramine-T method described by Dower et al. (*Nature* 324:266, 1986) and Segal et al. (*J. Immunol* 118:1338, 1977). In this procedure, 10 μg rIL-1α (0.57 nmol) in 10 μl phosphate (0.05 M) buffered saline (0.15 M) pH 7.2 (PBS) are added to 2.5 mCi (1.0 nmol) of sodium iodide in 25 μl of 0.05 M sodium phosphate pH 7.0. The reaction is initiated by addition of 30 μl of 1.4×10$^{-4}$ M chloramine-T (4.2 nmol; Sigma Chemical Co., St. Louis, Mo.). After 30 minutes on ice the reaction mixture is fractionated by gel filtration on a 1 ml bed volume Biogel P6 (Bio-Rad, Richmond, Calif.) column. Routinely, 40%–50% of $^{125}$I is incorporated into protein.

$^{125}$I-IL-1α a can be purified by gel filtration or other suitable methods and immediately diluted to a working stock solution of 3×10$^{-8}$ M in Roswell Park Memorial Institute (RPMI) 1640 medium comprising 1% (w/v) bovine serum albumin (BSA), 0.1% (w/v) sodium azide, 20 mM Hepes pH 7.4 (binding medium), to avoid radiolysis. Such dilute solutions can be stored for up to one month without detectable loss of receptor binding activity. The specific activity is routinely in the range 1–3×10$^{15}$ cpm/mmole (ca 1 atom of iodine per IL-1α molecule). Typically, the labeled protein is initially (prior to dilution) 100% active as determined by its capacity to elicit IL-2 production from EL4 6.1 C10 cells. Further, 100% of the $^{125}$I cpm can be precipitated by trichloroacetic acid and >95% can be absorbed by IL-1 receptor bearing cells.

EL-4 6.1 C10 cells are propagated in suspension culture as described by MacDonald et al., *J. Immunol.* 135:3964, 1985. An IL-1 receptor negative variant line of EL-4 cells, EL-4 (M) (ATCC TIB 39), is grown in an identical fashion. Cells are monitored on a weekly basis for IL-1 receptor expression by $^{125}$I-IL-1α receptor bearing cells.

To maintain relatively high levels of receptor expression, cells can be sorted using fluorescence-activated cell sorting (FACS) and fluorescein-conjugated recombinant IL-1α. Fluorescein-conjugated rIL-1α (FITC IL-1α) is prepared by reacting 2.9 nanomoles protein with 100 nanomoles of fluorescein isothiocyanate (Research Organics, Cleveland, Ohio) in a total volume of 70 μl of orate (0.02 M) buffered saline (0.15 M) pH 8.5 for two hours at 37° C. Protein is separated from unconjugated dye by gel filtration on a 1 ml bed volume P6 column, as described by Dower et al. (*J. Exp. Med* 162:501, 1985). Using an EPICS C flow cytometer (Coulter Instruments; 488 nM argon laser line, 300 MW, gain 20, PMT voltage 1700), cells providing the highest level fluorescence signal (e.g., the top 1.0% or 0.1%, as desired) are collected and used to establish cell cultures for receptor expression.

For extractions, cells harvested from culture by centrifugation are washed once with binding medium and sedimented at 2000×g for 10 min. to form a packed pellet (ca 8×10$^8$ cells/ml). To the pellet is added an equal volume of PBS containing 1% Triton X-100 and a cocktail of protease inhibitors (2 mM phenylmethylsulphonyl fluoride, 1 μM pepstatin, 1 μM leupeptin, and 2 mM O-phenanthroline). The cells are mixed with the extraction buffer by vigorous vortexing and the mixture incubated on ice for 15 minutes; at the end of this time the mixture is centrifuged at 11,000×g for 30 minutes at 8° C. to remove nuclei and other debris. The supernatant is made 0.02% w/v in sodium azide and stored either at 8° C. or −70° C., with no loss in IL-1 receptor activity detected for periods of up to six months at either temperature.

For solid phase binding assays, unless otherwise indicated, 1 μl (4×10$^5$ cell equivalents) aliquots of extract are placed on dry BA85/21 nitrocellulose membranes (Schleicher & Schuell, Keene, N. H.) and the membranes kept at room temperature until dry. Dry membranes can be stored at room temperature until use. Under these conditions, receptor binding activity remains stable for up to two months. Prior to use, membranes are reconstituted by incubating for 30 minutes in Tris (0.05 M) buffered saline (0.15 M) pH 7.5 containing 3% w/v BSA to block nonspecific binding sites, washed twice with PBS (20 ml per filter), once with binding medium and cut while wet into 0.9×0.9 cm squares with the IL-1 receptor extract at the center. The squares are placed in 24 well trays (Costar, Cambridge, Mass.) and covered with 200 $\mu$l of binding medium containing $^{125}$I-IL-1$\alpha$ or $^{125}$I-IL-1$\alpha$ and unlabeled inhibitors. Trays are then placed on a nutator and incubated in a refrigerator (8° C.) for two hours. At the end of this time a 60 $\mu$l aliquot can be taken from each well for determination of unbound $^{125}$I-rIL-1$\alpha$. Subsequently, the remaining solution is aspirated and discarded and the nitrocellulose filters washed by adding and aspirating sequentially 1 ml of binding medium and three times 1 ml of PBS to each well. The nitrocellulose squares are then removed and dried on filter paper. Subsequently, they are either placed on Kodak X-Omat AR film for twelve hours at −70° C., or placed in 12×75 cm glass tubes and counted on a gamma counter.

Definitions

"Interleukin-1 receptor" and "IL-1R" refer to proteins which are capable of binding Interleukin-1 (IL-1) molecules and, in their native configuration as mammalian plasma membrane proteins, presumably play a role in transducing the signal provided by IL-1 to a cell. As used herein, the term includes analogs of native proteins with IL-1 binding or signal transducing activity. Specifically included are truncated or soluble forms of the IL-1 receptor protein not having a cytoplasmic and transmembrane region. The predicted molecular weight of the murine protein corresponding to the sequence of the mature protein depicted in FIGS. 3A–3B is 64,597 daltons, while the predicted weight of the precursor is 66,697 daltons. Both of these estimates are exclusive of any glycosylation. The predicted molecular weight of the human protein corresponding to the sequence of the mature protein depicted in FIGS. 5A–5C is 63,486 daltons, while the predicted weight of the precursor is 65,402 daltons.

"Recombinant," as used herein, means that a protein is derived from recombinant (e.g., microbial or mammalian) expression systems. "Microbial" refers to recombinant proteins made in bacterial or fungal (eg., yeast) expression systems. As a product, "recombinant microbial" defines a protein essentially free of native endogenous substances and unaccompanied by associated native glycosylation. Protein expressed in most bacterial cultures, e.g., *E. coli,* will be free of glycan; protein expressed in yeast may have a glycosylation pattern different from that expressed in mammalian cells.

"Biologically active," as used throughout the specification as a characteristic of IL-1 receptors, means either that a particular molecule shares sufficient amino acid sequence similarity with the embodiments of the present invention disclosed herein to be capable of binding at least 0.01 nmoles IL-1 per nanomole IL-1 receptor or IL-1 receptor analog, or, in the alternative, shares sufficient amino acid sequence similarity to be capable of transmitting an IL-1 stimulus to a cell, for example, as a component of a hybrid receptor construct. Preferably, biologically active IL-1 receptors within the scope of the present invention are capable of binding greater than 0.1 nanomoles IL-1 per nanomole receptor, and most preferably, greater than 0.5 nanomoles IL-1 per nanomole receptor.

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. However, it will be evident that genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention are assembled from cDNA fragments and short oligonucleotide linkers, or from a series of oligonucleotides, to provide a synthetic gene which is capable of being expressed in a recombinant transcriptional unit.

"Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as *E. coli* or yeast such as *S. cerevisiae,* which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Isolation of cDNAs Encoding IL-1 Receptors

In order to secure the murine coding sequence, a DNA sequence encoding murine IL-1R (mIL-1R) was isolated from a cDNA library prepared by reverse transcription of polyadenylated RNA isolated from the murine cell line EL-4 6.1 C10. The library was screened by direct expression of pooled cDNA fragments in monkey COS-7 cells using a mammalian expression vector (pDC201) that uses regulatory sequences derived from SV40 and Adenovirus 2. Transfectants expressing biologically active IL-1R were identified by incubating transfected COS-7 cells with medium containing $^{125}$I-IL-1α, washing the cells to remove unbound labeled IL-1α, and contacting the cell monolayers with X-ray film to detect concentrations of IL-1α binding. Transfectants detected in this manner appear as dark foci against a relatively light background.

Using this approach, approximately 150,000 cDNAs were screened in pools of approximately 350 cDNAs until assay of one transfectant pool indicated positive foci of IL-1α binding. A frozen stock of bacteria from this positive pool was grown in culture and plated to provide individual colonies, which were screened until a single clone (clone 78) was identified which directed synthesis of a surface protein with detectable IL-1 binding activity. This clone was isolated, and its insert sequenced to determine the sequence of the murine cDNA set forth in FIG. 2. The initiator methionine for the full-length translation product of the native murine gene is one of two alternative methionine residues found at positions −19 and −16 of FIG. 3A. The first amino acid residue of the mature receptor protein was deduced by comparison to an N-terminal amino acid sequence obtained from highly purified preparations of IL-1R derived from EL-4 6.1 C10 cells. This residue is a leucine residue shown at position 1 of FIG. 3A The 1671 nucleotide coding region corresponding to the mature protein encodes 576 amino acids, including 15 cysteine residues and a 21-amino acid putative transmembrane region. Located N-terminal to the transmembrane region are 7 potential N-glycosylation sites. A cloning vector comprising the full-length murine cDNA, designated GEMBL78, has been deposited with the American Type Culture Collection (ATCC), Rockville, Md., accession no. 67563. The deposit was made under the conditions of the Budapest Treaty.

A probe was constructed from the murine sequence and used to screen human cDNA libraries prepared from cultures of a human T-cell clone grown in the presence of OKT3 antibody and IL-2. cDNA clones which hybridized to the murine probe were then isolated and sequenced. Using a fragment derived from human cDNA clones, a 1707 nucleotide human coding sequence was obtained and sequenced. The nucleotide sequence of the human cDNA, including 5' and 3' nontranslated sequences, is shown in FIG. 4. The nucleotide sequence of the human open reading frame and derived amino acid sequence of the human protein is set forth in FIGS. 5A–5C. This sequence comprises 569 amino acids (including a 17 amino acid signal peptide), including 16 cysteine residues, 13 of which are conserved between the murine and human genes. In addition, the human sequence includes six potential N-glycosylation sites, of which 5 are conserved between murine and human. The amino acid sequence of FIGS. 5A–5C is numbered from a leucine residue considered to be the likely N-terminus on the basis of comparison to the murine protein. The putative transmembrane region of the human gene is 20 amino acids in length. The sequences of the presumed intracellular portions of the murine and human genes are highly (87%) conserved; the extracellular (78%) and transmembrane regions (63%) are somewhat less conserved, except for the location of cysteines presumably involved in intramolecular disulfide bonding and certain N-glycosylation sites. The derived amino acid sequences of the human and murine genes are compared in FIG. 8.

The murine and human genes encode integral membrane proteins including intracellular regions having no apparent homology with any known protein sequence and extracellular portions which appear to be organized into domains similar to those of members of the immunoglobulin gene superfamily. Immunoglobulin-like domains typically possess only minimal amino acid similarity but share a common three-dimensional structure consisting of two β-sheets held together by a disulfide bond. The cysteine residues involved in formation of this disulfide bond, as well as a few other critical residues, are highly conserved and occur in the same relative position in almost all members of the family. Members of the immunoglobulin superfamily include not only immunoglobulin constant and variable regions but also a number of other cell surface molecules, many of which are involved in cell-cell interactions.

Like most mammalian genes, mammalian IL-1Rs are presumably encoded by multi-exon genes. Alternative mRNA constructs which can be attributed to different mRNA splicing events following transcription, and which share large regions of identity or similarity with the cDNAs claimed herein, are considered to be within the scope of the present invention.

In its nucleic acid embodiments, the present invention provides DNA sequences encoding mammalian IL-1Rs. Examples of mammalian IL-1Rs include primate IL-1R, human IL-1R, murine, canine, feline, bovine, ovine, equine and porcine IL-1Rs. IL-1R DNAs are preferably provided in a form which is capable of being expressed in a recombinant transcriptional unit under the control of mammalian, microbial, or viral transcriptional or translational control elements. For example, a sequence to be expressed in a microorganism will contain no introns. In preferred aspects, the DNA sequences comprise at least one, but optionally more than one sequence component derived from a cDNA sequence or copy thereof Such sequences may be linked or flanked by DNA sequences prepared by assembly of synthetic oligonucleotides. However, synthetic genes assembled exclusively from oligonucleotides could be constructed using the sequence information provided herein. Exemplary sequences include those substantially identical to the nucleotide sequences depicted in FIGS. 3A–3C. Alternatively, the coding sequences may include codons encoding one or more additional amino acids located at the N-terminus, for example, an N-terminal ATG codon specifying methionine linked in reading frame with the nucleotide sequence. Due to code degeneracy, there can be considerable variation in nucleotide sequences encoding the same amino acid sequence; exemplary DNA embodiments are those corresponding to the sequence of nucleotides 1–1671 of FIGS. 3A–3C, and nucleotides 1–1656 of FIGS. 5A–5C. Other embodiments include sequences capable of hybridizing to the sequence of FIGS. 3A–3C or 5A–5C under moderately stringent conditions (50° C., 2×SSC) and other sequences degenerate to those described above which encode biologically active IL-1R polypeptides.

The present invention also provides expression vectors for producing useful quantities of purified IL-1R. The vectors can comprise synthetic or cDNA-derived DNA fragments encoding mammalian IL-1Rs or bioequivalent homologues operably linked to regulatory elements derived from mammalian, bacterial, yeast, bacteriophage, or viral genes. Useful regulatory elements are described in greater detail below. Following transformation, transfection or infection of appropriate cell lines, such vectors can be induced to express recombinant protein.

Mammalian IL-1Rs can be expressed in mammalian cells, yeast, bacteria, or other cells under the control of appropriate promoters. Cell-free translation systems could also be employed to produce mammalian IL-1R using RNAs derived from the DNA constructs of the present invention. Appropriate cloning and recombinant expression vectors for use with bacterial, fungal, yeast, and mammalian cellular hosts are described by Pouwels et al. (*Cloning Vectors: A Laboratory Manual,* Elsevier, N.Y. 1985), the relevant disclosure of which is hereby incorporated by reference.

Various mammalian cell culture systems can be employed to express recombinant protein. Examples of suitable mammalian host cell lines include the COS-7 lines of monkey kidney cells, described by Gluzman (*Cell* 23:175, 1981), and other cell lines capable of expressing an appropriate vector, for example, the C127, 3T3, CHO, HeLa and BHK cell lines. Mammalian expression vectors may comprise non-transcribed elements such as an origin of replication, a suitable promoter and enhancer, and other 5' or 3' flanking nontranscribed sequences, and 5' or 3' nontranslated sequences, such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Additional details regarding the use of a mammalian high expression vector to produce a recombinant mammalian IL-1R are provided in Examples 4 and 6, below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Molecular Immunol.* 23:935, 1986).

Yeast systems, preferably employing Saccharomyces species such as *S. cerevisiae,* can also be employed for expression of the recombinant proteins of this invention. Yeast of other genera, for example, Pichia or Kluyveromyces, have also been employed as production strains for recombinant proteins.

Useful recombinant expression vectors for bacterial use are constructed by inserting a DNA sequence encoding mammalian IL-1R together with suitable translation initiation and termination signals in operable reading phase with a functional promoter. The vector will comprise one or more phenotypic selectable markers and an origin of replication to ensure amplification within the host. Suitable prokaryotic hosts for transformation include *E. coli, Bacillus subtilis, Salmonella typhimurium,* and various species within the genera Pseudomonas, Streptomyces, and Staphylococcus, although others may also be employed as a matter of choice.

Expression vectors are conveniently constructed by cleavage of cDNA clones at sites close to the codon encoding the N-terminal residue of the mature protein. Synthetic oligonucleotides can then be used to "add back" any deleted sections of the coding region and to provide a linking sequence for ligation of the coding fragment in appropriate reading frame in the expression vector, and optionally a codon specifying an initiator methionine.

Preferably, purified mammalian IL-1Rs or bioequivalent homologues are prepared by culturing suitable host/vector systems to express the recombinant translation products of the synthetic genes of the present invention, which are then purified from culture media.

An alternative process for producing purified IL-1R involves purification from cell culture supernatants or extracts. In this approach, a cell line which elaborates useful quantities of the protein is employed. Supernatants from such cell lines can be optionally concentrated using a commercially available protein concentration filter, for example, an Amicon or Millipore Pellicon ultrafiltration unit. Following the concentration step, the concentrate can be applied to a suitable purification matrix as previously described. For example, a suitable affinity matrix can comprise an IL-1 or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify an IL-1R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian IL-1R can be disrupted by any convenient method, including freeze-thaw cycling, sonication, mechanical disruption, hor use of cell lysing agents.

Fermentation of yeast which express mammalian IL-1R as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Numerous DNA constructions including all or part of the nucleotide sequences depicted in FIGS. 3A–3C or 5A–5C, in conjunction with oligonucleotide cassettes comprising additional useful restriction sites, can be prepared as a matter of convenience. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. By way of example, Walder et al. (*Gene* 42:133, 1986); Bauer et al. (*Gene* 37:73, 1985); Craik (*Biotechniques, pp.* 12–19, 1985); Smith et al. (*Genetic Engineenng. Principles and Methods,* Plenum Press, 1981); and U.S. Pat. No. 4,518,584 discloses suitable techniques, and are incorporated by reference herein.

Antibodies

Purified IL-1 receptor may be utilized to prepare both monoclonal and polyclonal antibodies, as well as other binding proteins which may be specifically constructed utilizing recombinant DNA methods. These binding proteins incorporate the variable regions from a gene which encodes a specifically binding monoclonal antibody. Within the context of the present invention, monoclonal antibodies and binding proteins are defined to be specifically binding if they bind with a $K_a$ of greater than or equal to $10^7$ $M^{-1}$. The affinity of a monoclonal antibody or binding protein may be readily determined by one of ordinary skill in the art (see Dower et al., "The Interaction of Monoclonal Antibodies with MHC Class I Antigens on Mouse Spleen Cells. I. Analysis of the Mechanism of Binding," *J. Immunol.* 132:751, 1984). Briefly, increasing amounts of radiolabeled antibody or binding protein are exposed to IL-1R bearing cells. An antibody's affinity may be determined by taking the reciprocal of the antibody concentration at which one-half of the antibodies maximally bind (see Dower et al., supra). As will be evident to one of ordinary skill in the art, antibodies may be generated against either whole IL-1R, or portions of the IL-1R. Particularly preferred are antibodies developed against the soluble truncated form of the IL-1R. Additionally, within the context of the present invention monoclonal antibodies include F(ab')$_2$ and Fab fragments which may be readily prepared by one of ordinary skill in the art.

Polyclonal antibodies may be readily generated by one of ordinary skill in the art from a variety of warm-blooded animals such as horses, cows, various fowl, rabbits, mice, or rats. Briefly, IL-1R is utilized to immunize the animal through intraperitoneal, intramuscular, intraocular, or subcutaneous injections. The immunogenicity of IL-1R may be increased through the use of an adjuvant such as Freund's complete or incomplete adjuvant. Following several booster immunizations, small samples of serum are collected and tested for reactivity to IL-1R by any of a number of methods, including among others, assays discussed below in the Examples such as an ELISA, ABC or modified ABC assays, or by a dot blot assay. Particularly preferred polyclonal antisera will give a signal on one of these assays that is at least three times greater than background. Once the titer of the animal has reached a plateau in terms of its reactivity to the IL-1R, larger quantities of polyclonal antisera may be readily obtained either by weekly bleedings, or by exsanguinating the animal.

Monoclonal antibodies may also be readily generated using conventional techniques (see U.S. Pat. No. RE 32,011, U.S. Pat. Nos. 4,902,614, 4,543,439, and 4,411,993 which are incorporated herein by reference; see also *Monoclonal Antibodies, Hybridomas: A New Dimension in Biological Analyses,* Plenum Press, Kennett, McKearn, and Bechtol (eds.), 1980, and *Antibodies: A Laboratory Manual,* Harlow and Lane (eds.), Cold Spring Harbor Laboratory Press, 1988, which are also incorporated herein by reference). Briefly, within one embodiment a subject animal such as a rat or mouse is injected with a form of IL-1R suitable for generating an immune response against the IL-1R. This may be accomplished by immunization with various forms of the IL-1R, including among others, cells which express the IL-1R, viruses such as the vaccinia virus which express the IL-1R, soluble forms of the IL-1R, or peptides which are based upon the IL-1R sequence. Additionally, many techniques are known in the art for increasing the resultant immune response, for example by coupling the soluble receptor or peptide to another protein such as ovalbumin or keyhole limpet hemocyanin (KLH), or through the use of adjuvants such as Fruend's complete or incomplete adjuvant. The initial immunization may be through intraperitoneal, intramuscular, intraocular, or subcutaneous routes.

Between one and three weeks after the initial immunization the animal may be reimmunized with another booster immunization. The animal may then be test bled and the serum tested for immunoreactivity to the IL-1R using assays such as an ELISA, dot blot, ABC or modified ABC assay as described below in the Examples. Additional immunizations may also be accomplished until the animal has plateaued in its reactivity to the IL-1R. The animal may then be given a final boost of soluble IL-1R, and three to four days later sacrificed. At this time, organs which contain large numbers of B cells such as the spleen and lymph nodes may be harvested and disrupted into a single cell suspension by passing the organs through a mesh screen or by rupturing the spleen or lymph node membranes which encapsidate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed and the spleen and lymph node cells are removed as described above. A single cell suspension is prepared, and the cells are placed into a culture which contains a form of the IL-1R, which is suitable for generating an immune response as described above. Subsequently, the lymphocytes are harvested and fused as described below.

Cells which are obtained through the use of in vitro immunization or from an immunized animal as described above may be immortalized by transfection with a virus such as the Epstein bar virus (EBV) (see Glasky and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas,* 6th ed., ATCC, 1988). Representative myeloma lines include: for humans UC 729-6 (ATCC No. CRL 8061), MC/CAR-Z2 (ATCC No. CRL 8147), and SKO-007 (ATCC No. CRL 8033); for mice SP2/0-AG14 (ATCC No. CRL 1581), and P3X63Ag8 (ATCC No. TIB 9), and for rats Y3-Ag1.2.3 (ATCC No. CRL 1631), and YB2/0 (ATCC No. CRL 1662). Particularly preferred fusion lines include NS-1 (ATCC No. TIB 18), and P3X63-Ag 8.653 (ATCC No. CRL 1580) which may be utilized for fusions with either mouse, rat, or human cell lines. Fusion between the myeloma cell line and the cells from the immunized animal may be accomplished by a variety of methods, including the use of polyethylene glycol (PEG) (see *Antibodies: A Laboratory Manual,* Harlow and Lane (eds.), Cold Spring Harbor Laboratory Press, 1988) or electrofusion (see Zimmerman and Vienken, *J. Membrane Biol.* 67:165–182, 1982).

Following the fusion, the cells may be placed into culture plates containing a suitable medium, such as RPMI 1640, or DMEM (Dulbecco's Modified Eagles Medium) (JRH Biosciences, Lenexa, Kans.). The medium may also contain additional ingredients, such as Fetal Bovine Serum (FBS, i.e., from Hyclone, Logan, Utah, or JRH Biosciences), thymocytes which were harvested from a baby animal of the same species as was used for immunization, or agar to solidify the medium. Additionally, the medium should contain a reagent which selectively allows for the growth of fused spleen and myeloma cells. Particularly preferred is the use of HAT (hypoxanthine, aminopterin, and thymidine)

(Sigma Chemical Co., St. Louis, Mo.). After about seven days, the resulting fused cells or hybridomas may be screened as described below in Example 15 in order to determine the presence of antibodies which recognize IL-1R. Following several clonal dilutions and reassays, a hybridoma producing antibodies which bind to IL-1R may be isolated.

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, August 1989; see also Michelle Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, binding proteins may also be constructed utilizing recombinant DNA techniques to incorporate the variable regions of a gene which encodes a specifically binding antibody. The construction of these proteins may be readily accomplished by one of ordinary skill in the art (see James W. Larrick et al., "Polymerase Chain Reaction Using Mixed Primers: Cloning of Human Monoclonal Antibody Variable Region Genes From Single Hybridoma Cells," *Biotechnology* 7:934–938, September 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989), given the disclosure provided herein. Briefly, the antigen-binding sites or IL-1 receptor binding domain from a cell which produces a specifically binding monoclonal antibody are amplified, and inserted directly into the genome of a cell which produces human antibodies (see Verhoeyen et al., supra; see also Reichmann et al., supra). This technique allows the antigen-binding site of a specifically binding murine or rat monoclonal antibody to be transferred into a human antibody. Such antibodies are preferable for therapeutic use in humans because they are not as antigenic as rat or mouse antibodies. Alternatively, the antigen-binding sites (variable region) may be either linked to, or inserted into, another completely different protein (see Chaudhary et al., supra), resulting in a new protein with antigen-binding sites of the antibody as well as the functional activity of the completely different protein. As one of ordinary skill in the art will recognize, the antigen-binding sites or IL-1 receptor binding domain of the antibody may be found in the variable region of the antibody. Furthermore, DNA sequences which encode smaller portions of the antibody or variable regions which specifically bind to mammalian IL-1R may also be utilized within the context of the present invention. These portions may be readily tested for binding specificity to the IL-1R utilizing assays described below in Example 15, including for example ELISA, ABC, or dot blot assays.

Within a preferred embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers may be utilized to amplify heavy or light chain variable regions, which may then be inserted into vectors such as ImmunoZAP™ or ImmunoZAP™ L (Stratacyte), respectively. These vectors may then be introduced into *E. coli* for expression. Utilizing these techniques, large amounts of a single-chain protein containing a fusion of the $V_H$ and $V_L$ domains may be produced (see Bird et al., *Science* 242:423–426, 1988).

Within another embodiment, the binding protein is fused within the expression vector to another protein, such as a toxin. Cells which are bound by the binding protein may thus be killed by incorporation of the toxin (see Chaudhary et al.). Alternatively, the binding protein may be fused to an IL-1 antagonist (i.e., a protein which binds IL-1 receptor but generates no biological activity), allowing large local concentrations of the antagonist to be developed around cells which express IL-1 receptor. Only cells which could bind the antagonist would be affected, potentially decreasing the dose needed for therapeutic purposes.

Once suitable antibodies or binding proteins have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Antibodies and binding proteins of the present invention have many uses. For example, antibodies may be utilized in flow cytometry to sort IL-1R bearing cells, or to histochemically stain IL-1R bearing cells. Briefly, in order to detect IL-1 receptors on cells, the cells are incubated with a labeled monoclonal antibody which specifically binds to mammalian IL-1 receptors, followed by detection of the presence of bound antibody. These steps may also be accomplished with additional steps such as washings to remove unbound antibody. Labels suitable for use within the present invention are well known in the art including, among others, Flourescein Isothiocyanate (FITC), Phycoerythrin (PE), Horse Radish Peroxidase (HRP), and colloidal gold. Particularly preferred for use in flow cytometry is FITC which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; and Goding, "Conjugation of Antibodies with Fluorochromes: Modification to the Standard Methods," *J. Immunol. Methods* 13:215–226, 1970.) For histochemical staining, HRP is preferred, which may be conjugated to the purified antibody according to the method of Nakane and Kawaoi in "Peroxidase-Labeled Antibody: A New Method of Conjugation," *J. Histochem. Cytochem.* 22:1084–1091, 1974. (See also Tijssen and Kurstak, "Highly Efficient and Simple Methods for Preparation of Peroxidase and Active Peroxidase Antibody Conjugates for Enzyme Immunoassays," *Anal. Biochem.* 136:451–457, 1984.)

Purified antibodies or binding proteins may also be utilized therapeutically to block the binding of IL-1 to the receptor in vivo, or for in vivo neutralization of IL-1R bearing cells. Within preferred embodiments, the antibody is modified to escape immunological detection, for example, by transferring the antigen-binding site of a specific murine monoclonal antibody to a human monoclonal antibody, as discussed above. Particularly preferred is the use of therapeutic compositions comprising an antibody or binding protein to the IL-1 receptor, and a physiologically acceptable carrier or diluent. Suitable carriers or diluents include, among others, neutral buffered saline or saline mixed with nonspecific albumin. Additionally, the therapeutic composition may include further excipients or stabilizers such as buffers, carbohydrates including, for example, glucose, sucrose, or dextrose, chelating agents such as EDTA, or various preservatives. Appropriate dosages may be determined in clinical trials, although the amount and frequency of administration may be dependent on such factors as the nature and severity of the indication being treated, the desired response, and the condition of the patient.

Antibodies may also be utilized to monitor the presence of circulating soluble IL-1R which has been administered to a patient, or to measure in vivo levels of IL-1R in patients. Within a preferred embodiment, a double determinant or sandwich assay is utilized to detect the IL-1R. Briefly, serum suspected of containing soluble IL-1R is incubated with a solid support having a monoclonal antibody, as described above, affixed thereto under conditions and for a time sufficient for binding to occur. Many solid supports are known in the art, including, among others, ELISA plates (Linbro, McLean, Va.), nitrocellulose (Millipore Corp. Bedford, Mass.), beads (Polysciences, Warrington, Pa.), and magnetic beads (Robbin Scientific, Mountain View, Calif.). Additionally, the monoclonal antibody may be readily affixed to the solid support utilizing techniques well known in the art (see *Antibodies: A Laboratory Manual,* Harlow and Lane (eds.), Cold Spring Harbor Laboratory Press, 1988). The solid support is then incubated with a second labeled monoclonal antibody specific for mammalian IL-1 receptors under conditions and for a time sufficient for binding to occur, after which presence of bound labeled antibody may be detected.

Within a particularly preferred embodiment, a monoclonal antibody is coated onto a solid support such as a 96 well plate. Subsequently, the plate is blocked with a protein such as bovine serum albumin or nonfat dry milk for about 30 minutes. Serum from a patient is diluted in phosphate buffered saline and incubated in the wells under conditions and for a time sufficient for binding to occur—generally about 30 minutes. Subsequently, the plate is washed and a labeled second monoclonal antibody specific for a different IL-1R epitope is added into the wells and incubated as described above. Antibodies for different IL-1R may be determined through the use of cross-blocking assays, as described below in Example 15. The well is then examined for the presence of the second labeled antibody. Presence of the second labeled antibody indicates the presence of the IL-1R in the patient's serum. As will be understood by one of ordinary skill in the art, the monoclonal antibodies used within the above assay may be substituted with polyclonal antibodies or binding proteins which are specific for the IL-1 receptor.

The following examples are offered by way of illustration, and not by way of limitation.

EXAMPLES

Example 1

Preparation of IL-1α Affinity Matrix and Affinity Purification of Receptor from Surface Labeled EL-4 6.1 C10 Cells Cell surface proteins on EL 46.1 C10 cells were radiolabeled with $^{125}$I by the glucose oxidase-lactoperoxidase method disclosed by Cosman et al. (*Molecular Immunol.* 23:935, 1986). Labeled cells were pelleted by centrifugation, washed three times with PBS, and extracted with PBS containing 1% Triton X-100 and the cocktail of protease inhibitors described in the assay protocol detailed above. The Triton X-100 extract was spun for 10 minutes in an Eppendorf microcentrifuge and the supernatant was stored at −70° C.

Recombinant IL-1α was coupled to cyanogen bromide activated Sepharose 4B (Pharmacia, Piscataway, N.J., USA) or to Affigel-10 (Bio-Rad, Richmond, Calif., USA) according to the manufacturer's suggestions. For example, to a solution of IL-1α (1.64 mg/ml in 9.5 ml PBS), 3 ml were added of swollen, acid-washed, CNBr-activated Sepharose. The solution was rocked overnight at 4° C. and an aliquot of the supernatant was tested for protein by a fluorescamine protein assay as described by Udenfriend et al. (*Science* 178:871, 1972), using BSA as a standard. Ninety-eight percent of the protein had coupled to the gel, suggesting that the column had a final load of 5.1 mg IL-1α per ml gel. Three hundred μl of 1 M glycine-ethyl-ester (Sigma Chemical Co., St. Louis, Mo., USA) were added to the slurry to block any unreacted sites on the gel.

The gel was washed extensively with 0.1 M glycine buffer pH 3.0 containing 0.1% Triton X-100, PBS containing 0.1% Triton X-100, RIPA buffer (0.05 M Tris-HCl pH 7.5, 0.15 M NaCl, 1% NP40, 1% sodium deoxycholate, 0.1% SDS), and PBS containing 0.1% Triton X-100 and 10 mM ATP. Small columns (200 μl) were prepared in disposable polypropylene holders (Bio-Rad, Richmond, Calif., USA) and washed with PBS containing 1% Triton X-100. Aliquots of 100 μl of $^{125}$I-labeled extract were applied to a column, which was then washed with PBS containing 1% Triton X-100, RIPA buffer, PBS containing 0.1% Triton X-100 and 10 mM ATP, and PBS with 1% Triton X-100.

The IL-1 receptor on murine T cells is a robust structure capable of binding $^{125}$I-IL-1α in Triton X-100 detergent solutions. To be able to recover receptor from such an affinity matrix, a mild elution procedure is necessary. Mild acid treatment can cause rapid dissociation of preformed IL-1α/IL-1 receptor complexes. Based upon this observation, pH 3.0 glycine HCl buffer containing 0.1% Triton X-100 were used to elute receptor from the IL-1α affinity columns, which was collected in 0.05 ml fractions. The presence of receptor in the fractions was detected by dot blot as described above, using $^{125}$I-labeled IL-1α.

Analysis by SDS-PAGE proceeded as follows. To 50 μl of each column fraction was added 50 μl of 2×SDS sample buffer (0.125 M Tris HCl pH 6.8, 4% SDS, 20% glycerol, 10% 2-mercaptoethanol). The solution was placed in a boiling water bath for three minutes and aliquots of 40 μl were applied to the sample well of a 10% polyacrylamide gel which was set up and run according to the method of Laemmli (*Nature* 227:680, 1970). Gels were fixed and stained using 0.25% Coomassie brilliant blue in 25% isopropanol, 10% acetic acid) destained in 25% isopropanol, 10% acetic acid, treated with Enhance (New England Nuclear, Boston, Mass., USA) dried and exposed to Kodak X-Omat AR film at −70° C. Molecular weight markers, labeled with $^{14}$C, were obtained from New England Nuclear, and included: cytochrome C ($M_r$ 12,300), lactoglobulin A ($M_r$ 18,367), carbonic anhydrase ($M_r$ 31,000,), ovalbumin ($M_r$ 46,000), bovine serum albumin ($M_r$ 69,000), phosphorylase B ($M_r$ 97,400) and myosin ($M_r$ 200,000). Alternatively, fractions having receptor activity were analyzed by SDS polyacrylamide gel electrophoresis followed by silver staining as previously described by Urdal et al. (*Proc. Natl. Acad. Sci. USA* 81:6481, 1984).

Dot blot analysis of fractions eluted from the IL-1α affinity matrix showed that IL-1 binding activity was detected in fractions that were collected after pH 3.0 glycine buffer was applied to the column. Fractions that scored positive in this assay, when analyzed by SDS-PAGE, revealed that a protein of $M_r$ 82,000 could be detected upon developing the gel with silver stain. To determine which of the proteins detected by silver stain were expressed on the cell surface, EL-4 6.1 cells were surface labeled with $^{125}$I by the lactoperoxidase-glucose oxidase procedure. Radiolabeled cells were then extracted with PBS containing 1% Triton X-100 and aliquots of the detergent extract applied to an IL-1α affinity matrix. Fractions that were collected from this column, following application to the column of pH 3.0 glycine buffer, contained a radiolabeled protein of $M_r$ 82,000.

Example 2

Comparison of Properties of Cellular IL-1 Receptor and IL-1 Receptor Isolated from Cell Extracts In a preliminary experiment, the binding properties of the IL-1 receptor were compared in intact EL4 6.1 C10 cells and after extraction from cells. $3.8×10^8$ EL-4 6.1 C10 cells were divided into two equal aliquots, one of which was extracted as described above. The remaining cells were resuspended at $3.8×10^7$ cells/ml and used for direct binding studies. Extract was adsorbed to nitrocellulose and used for solid phase binding studies employing various concentrations of $^{125}$I-IL-1α with or without unlabeled IL-1. After washing and drying, the nitrocellulose filters were first counted for bound $^{125}$I-IL-1α and subsequently placed on film for autoradiography. Nonspecific background was measured in the presence of $5.7×10^{-7}$ M unlabeled rIL-1β. The data obtained showed that $^{125}$I-IL-1α was bound to the extract on nitrocellulose in an IL-1 concentration-dependent fashion, and that the $^{125}$I-IL-1α was specifically bound to the region of the blot where extract is present. Further, binding could be extensively blocked by inclusion of unlabeled IL-1α in the incubation mixture.

The comparison further indicated that not only were the levels of receptor the same in both instances, but that the receptors after adsorption to nitrocellulose exhibited an affinity for ligand which was indistinguishable from that of the receptor in intact cells. No significant difference between the number of receptors detected on intact cells and those detected following detergent extraction was found. This is consistent with the view that the majority of the receptors were present on the external face of the plasma membrane in intact cells.

To measure the specificity of binding of IL-1 receptors on nitrocellulose filters, 2 μl of EL-4 6.1 C10 extract were applied to nitrocellulose filters, dried, blocked and assayed as described above. The following proteins were tested for their capacity to inhibit $^{125}$I-IL-1α binding: human rIL-1α ($7.62×10^{-7}$ M), human rIL-1β ($7.62×10^{-7}$ M), human IL-2 ($8.9×10^{-7}$ M), murine IL-3 ($7.5×10^{-4}$ M), murine-GM-CSF ($7.5×10^{-7}$ M), recombinant murine IL-4 ($5×10^{-9}$ M), human epidermal growth factor 3 μg/ml, fibroblast growth factor 1 μg/ml, rat submandibular gland nerve growth factor (2 μg/ml), bovine insulin ($1×10^7$ M), human luteinizing hormone 1 μg/ml), human growth hormone $1.7×10^{-7}$ ), thyroid stimulating hormone (1 μg/ml), and follicle stimulating hormone (1 μg/ml). All incubations were done with $1.9×10^{-10}$ M $^{125}$I-IL-1α.

This experiment demonstrated that extracted receptor retains the same specificity as that previously demonstrated for intact cells. As found with intact cells, only IL-1α and IL-1β produced any significant inhibition of $^{125}$I-IL-1α binding. The data showed that unlabeled IL-1α and IL-1β produced >90% inhibition of $^{125}$I-IL-1α binding, while no significant blockade was observed with any of the other hormones.

To determine whether receptor in detergent solution would bind IL-1 with an affinity equal to that of receptor in cell membranes, or adsorbed to nitrocellulose, a third experiment was performed in which the nitrocellulose dot blot binding assay was used to test the capacity of an EL-4 6.1 C10 extract in Triton X-100 solution to inhibit binding of $^{125}$I-IL-1α to the solid phase. EL-4 6.1 $C_{10}$ extracts were adsorbed to nitrocellulose, dried, blocked and incubated with mixture of $^{125}$I-IL-1α and extracts containing receptors in detergent solution.

The concentration of receptor in the solution phase was estimated from a saturation binding curve to 1 μl aliquots blotted on nitrocellulose, allowing receptors/μl to be calculated and hence IL-1 receptor concentration (M). The extract was diluted through PBS Triton X-100 solution (0.5% Triton) to keep the detergent concentration constant. The inhibition curve showed that in solution, the receptor bound to $^{125}$I-IL-1α with a $K_a$ ($4.5±0.5×10^9$ $M^{-1}$) that is the same as that of receptor on the solid phase or in membranes. Further, the close fit between the theoretical curve, which is based on a simple competitive inhibition model, and the data was consistent with the hypothesis that a single type of IL-1 binding protein was present in the membrane extract.

In order to examine the integrity of the receptor as a function of the concentration of total EL-4 6.1 C10 extract membrane proteins, a fourth experiment was done. Mixtures of EL-4 6.1 C10 extract in various proportions ranging from 10% to 100% were made either with an extract from cells not expressing the IL-1 receptor, EL-4 (M) cells, or with PBS Triton X-100 (0.5%). Each mixture was analyzed for receptor concentration, and affinity of $^{125}$I-IL-1α binding by quantitative dot blot binding. Receptor concentration decreased linearly with the percentage of EL-4 6.1 C10 extract present, whether membrane protein concentration was maintained at a constant level or not. In both series of mixtures the affinity of the receptor for $^{125}$I-IL-1α a remained constant. These data are consistent with one of two hypotheses, either the receptor binding function is contained within a single polypeptide chain or, if the functional receptor requires two or more subunits for IL-1 binding, these are sufficiently tightly associated that dilution through detergent does not separate them.

Example 3

Purification of IL-1 Receptor to Homogeneity and Determination of N-Terminal Sequence 300–500 liters of EL-4 6.1 C10 cells were grown to saturation under the conditions previously described, harvested, and extracted with PBS-1% Triton X-100. The detergent extract was applied to an IL-1α affinity column and the column washed as previously described. Fractions containing IL-1 receptor were detected by the $^{125}$I-IL1α dot blot procedure following elution of the column with 0.1 M glycine HCl pH 3.0 containing 0.1% Triton X-100. Aliquots of the fractions were analyzed by SDS polyacrylamide gel electrophoresis.

This partially purified IL-1 receptor composition prepared by affinity chromatography on Affigel-IL1α was adjusted to contain the following buffer composition: 10 mM Tris-HCl, pH 8, 250 mM NaCl, 0.5 mM $MgCl_2$, 0.5 mM $MnCl_2$, 0.5 mM $CaCl_2$, and 0.01% (v/v) Triton X-100 (WGA buffer). The IL-1 receptor composition was then applied to a 1 ml column of wheat germ agglutinin (WGA) bound to Sepharose CL-6B, equilibrated with WGA buffer. Following application of the IL-1 receptor composition, the WGA column was washed with 20 ml of WGA buffer followed by 10 mM Tris HCl, pH 8, 0.01% (v/v) Triton X-100. The IL-1 receptor protein was eluted from the WGA column with 10 mM Tris-HCl, pH 8, 0.5 M N-acetylglucosamine, and 0.01% (v/v) Triton X-100. The presence of biologically active IL-1 receptor was detected by the $^{125}$I-IL-1α dot blot procedure. The fractions were also analyzed by SDS polyacrylamide gel electrophoresis followed by silver staining.

Material eluting from the WGA column was applied to a C8 RP-HPLC column. The C8 RP-HPLC column (Brownlee Labs RP-300, 1 mm×50 mm) was previously equilibrated with 0.1% (v/v) trifluoroacetic acid (TFA) in HPLC grade $H_2O$, at a flow rate of 50 µl/min. Following application of the IL-1 receptor containing material, the C8 RP-HPLC column was washed with 0.1% (v/v) TFA in $H_2O$ at 50 µl/min until the absorbance at 280 nm returned to baseline. The IL-1 receptor protein was eluted from the column by running a linear gradient of 0.1% (v/v) TFA in acetonitrile from 0–100% at a rate of 1% per minute. Aliquots of the fractions were analyzed by SDS polyacrylamide gel electrophoresis. The IL-1 receptor protein was found to consist of a single band on an SDS polyacrylamide gel migrating with a molecular weight of 82,000.

The purified IL-1 receptor protein was analyzed by Edman degradation using an Applied Biosystems Model 470A protein sequencer. The protein (150 picomoles) was not modified before analysis. The results of the N-terminal protein sequence analysis of the IL-1 receptor indicated the following sequence of amino acid residues: NH$_2$-Leu-Glu-Ile-Asp-Val-Cys-Thr-Glu-Tyr-Pro-Asn-Gln-Ile-Val-Leu-Phe-Leu-Ser-Val-Asn-Glu-Ile-Asp-Ile-Arg-Lys.

This protein sequence was found to be unique when compared to the Mar. 17, 1987 release of the Protein Sequence Database of the Protein Identification Resource of the National Biomedical Research Foundation. This release of the database contained 4,253 sequences consisting of 1,029.056 residues.

Example 4

Isolation of cDNA Encoding Murine IL-1R by Direct Expression of Active Protein in COS-7 Cells A cDNA library was constructed by reverse transcription of polyadenylated mRNA isolated from total RNA extracted from EL-4 6.1 C10 cells by a procedure similar to that of Chirgwin et al. (*Biochem.* 18:5294, 1979). Briefly, the cells were lysed in a guanidinium isothiocyanate solution, and the lysate layered over a pad of CsCl and centrifuged until the RNA had pelleted. The RNA pellet was resuspended and further purified by protease digestion, organic extraction and alcohol precipitation. Poly A$^+$ RNA was isolated by oligo dT cellulose chromatography and double-stranded cDNA was prepared by a method similar to that of Gubler and Hoffman (*Gene* 25:263, 1983). Briefly, the RNA was copied into cDNA by reverse transcriptase using either oligo dT or random oligonucleotides as primer. The cDNA was made double-stranded by incubation with *E. coli* DNA polymerase I and RNase H, and the ends made flush by further incubation with $T_4$ DNA polymerase. The blunt-ended cDNA was ligated into SmaI-cut dephosphorylated pDC201 vector DNA The eukaryotic high expression vector pDC201 was assembled from SV40, adenovirus 2, and pBR322 DNA comprising, in sequence: (1) an SV40 fragment containing the origin of replication, early and late promoters, and enhancer; (2) an adenovirus 2 fragment containing the major late promoter, the first exon and part of the first intron of the tripartite late leader; (3) a synthetic sequence comprising a HindIII site, a splice acceptor site, the second and third exons of the adenovirus 2 tripartite leader and a multiple cloning site including a SmaI site: (4) additional SV40 sequences containing early and late polyadenylation sites; (5) adenovirus 2 sequences including the virus-associated RNA genes; and (6) pBR322 elements for replication in *E. coli.*

The resulting EL-4 6.1 C10 cDNA library in pDC201 was used to transform *E. coli* strain DH5α, and recombinants were plated to provide approximately 350 colonies per plate and sufficient plates to provide approximately 25,000 total colonies per screen. Colonies were scraped from each plate, pooled, and plasmid DNA prepared from each pool. The pooled DNA was then used to transfect a sub-confluent layer of monkey COS-7 cells using DEAE-dextran followed by chloroquine treatment, as described by Luthman et al. (*Nucleic Acids Res.* 11:1295, 1983) and McCutchan et al. (*J. Natl. Cancer Inst.* 41:351, 1986). The cells were then grown in culture for three days to permit transient expression of the inserted sequences. After three days, cell culture supernatants were discarded and the cell monolayers in each plate assayed for IL-1 binding as follows. Three ml of RPMI medium continuing 3×10$^{-10}$ M $^{125}$I-IL-1α was added to each plate and the plates incubated for 2 hours at 8° C. This medium was then discarded, and each plate was washed with 10 ml RPMI 1640 medium (containing no labeled IL-1α). The edges of each plate were then broken off, leaving a flat disk which was contacted with X-ray film for 72 hours at −70° C. using an intensifying screen. IL-1 binding activity was visualized on the exposed films as a dark focus against a relatively uniform background.

After approximately 150,000 recombinants from the library had been screened in this manner, one transfectant pool was observed to provide IL-1 binding foci which were clearly apparent against the background exposure.

A frozen stock of bacteria from the positive pool was then used to obtain plates of approximately 350 colonies. Replicas of these plates were made on nitrocellulose filters, and the plates were then scraped and plasmid DNA prepared and transfected as described above to identify a positive plate. Bacteria from individual colonies from the nitrocellulose replicas of this plate were grown in 2 ml cultures, which were used to obtain plasmid DNA, which was transfected into COS-7 cells as described above. In this manner, a single clone, clone 78, was isolated which was capable of inducing expression of IL-1R in COS cells. The insert was subcloned into a plasmid derived from pBR322 (GEMBL) and sequenced by conventional techniques. The sequence is set forth in FIG. 2.

Example 5

Isolation of Human cDNA Clones which Hybridize to Murine IL-1 Receptor Probe DNAs A cDNA polynucleotide probe was prepared from the 2,356 base pair (bp) fragment of clone 78 (see Example 4) by nick-translation using DNA polymerase I. The method employed was substantially similar to that disclosed by Maniatis et al. (supra, p. 109).

A cDNA library was constructed by reverse transcription of polyadenylated mRNA isolated from total RNA extracted from the cultured cells of a human T-cell line designated clone 22, described by Acres et al. (*J. Immunol.* 138:2132, 1987). These cells were cultured in RPMI 1640 medium plus 10% fetal bovine serum as described by Acres et al. (supra), in the presence of 10 ng/ml OKT3 antibody and 10 ng/ml human IL-2. The cDNA was rendered double-stranded using DNA polymerase I, blunt-ended with T4 DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., *DNA Cloning: A Practical Approach*, Glover (ed.), IRL Press, pp. 49–78). The ligated DNA was packaged into phage particles using a commercially available kit (Stratagene Cloning Systems, San Diego, Calif., USA 92121) to generate a library of recombinants. Recombinants were plated on *E. coli* strain C600(HFI⁻) and screened by standard plaque hybridization techniques under conditions of moderate stringency (50° C., 6×SCC).

Following several rounds of screening, nine clones were isolated from the library which hybridized to the cDNA probe. The clones were plaque purified and used to prepare bacteriophage DNA which was digested with EcoRI. The digests were electrophoresed on an agarose gel, blotted onto nylon filters, and retested for hybridization. The clones were digested with EcoRI followed by preparative agarose gel electrophoresis, then subcloned into an EcoRI-cut derivative (pGEMBL) of the standard cloning vector pBR322 containing a polylinker having a unique EcoRI site, a BamHI site and numerous other unique restriction sites. An exemplary vector of this type is described by Dente et al. (*Nucleic Acids Research* 11: 1645, 1983).

Restriction mapping and sequencing of a 4.8 kb human IL-1R clone indicated that the clone included a sequence encoding 518 amino acids which exhibited 80% amino acid sequence identity to the corresponding murine sequence in the extracellular, or N-terminal region distal to the transmembrane region, 63% identity in the transmembrane region, and 87% identity in the cytoplasmic, or C-terminal region. In addition, several cysteine residues and most N-linked glycosylation sites between the mouse and human sequences were conserved. A 440 bp EcoRI-NsiI fragment derived from the 5' portion of the human IL-1R clone was $^{32}$P-labeled by nick-translation as described above and used to screen a cDNA library produced by randomly-priming clone 22 mRNA prepared as described above. Twenty-three clones which hybridized to the probe were isolated and analyzed by restriction mapping. Sequencing of one of these clones provided the sequence information corresponding to the remaining N-terminal 34 amino acids of the human protein. The coding and deduced amino acid sequence of the complete coding region of human IL-1R is shown in FIGS. 5A–5C.

Example 6

Figure 6:
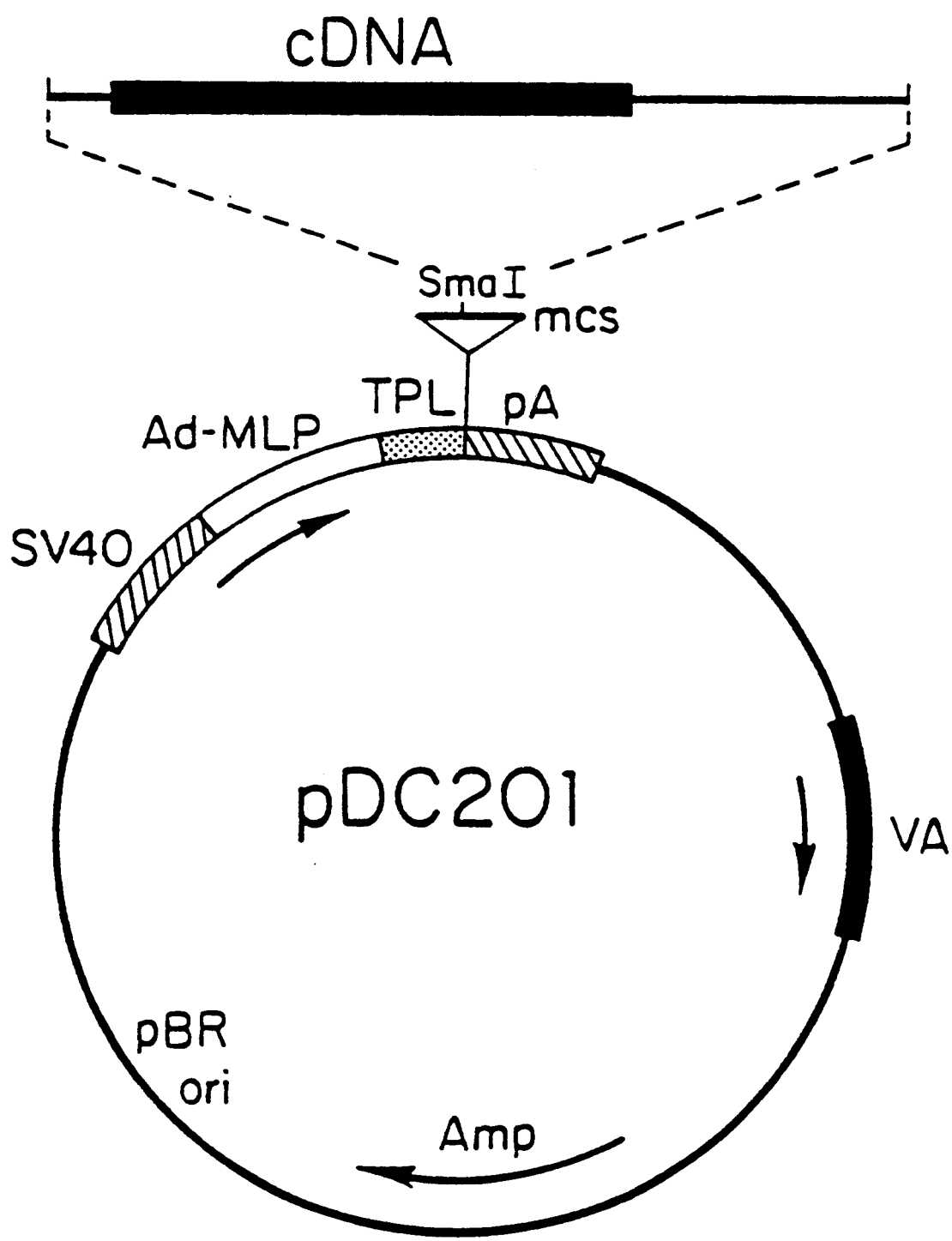
FIG. 6 is a schematic illustration of the mammalian high expression plasmid pCD201, which is described in greater detail in Example 6.

Expression of Recombinant IL-1 Receptor Using a High-Efficiency Mammalian Expression System The mammalian expression plasmid pDC201, depicted in FIG. 6, is designed to express cDNA sequences inserted at its multiple cloning site (MCS) when transfected into mammalian cells. Referring now to FIG. 6, pDC201 includes the following components: SV40 (hatched box) contains SV40 sequences from coordinates 5171–270 including the origin of replication, enhancer sequences and early and late promoters. The fragment is oriented so that the direction of transcription from the early promoter is as shown by the arrow. Ad-MLP (open box) contains adenovirus-2 sequences from coordinates 5779–6231 including the major late promoter, the first exon and part of the intron between the first and second exons of the tripartite leader. TPL (stippled box) contains a synthetic DNA sequence specifying adenovirus-2 sequences 7056–7172, 9634–9693 (containing the acceptor splice site of the second exon of the tripartite leader, the second exon and part of the third exon of the tripartite leader) and a multiple cloning site (MCS) containing sites for KpnI, SmaI, and BglII. pA (hatched box) contains SV40 sequences from 4127–4100 and 2770–2533 that include the polyadenylation and termination signals for early transcription. VA (solid box) contains adenovirus-2 sequences from 10226–11555 that include the virus-associated RNA genes (VAI and VAII). The solid lines are derived from pBR 322 and represent (starting after the pA sequences and proceeding clockwise) coordinates 29–23, 651–185 (at which point the VA sequences are inserted), 29–1, 4363–2486, and 1094–375. pDC201 is a derivative of pMLSV, previously described by Cosman et al., *Molec. Immunol.* 23:935, 1986.

To express recombinant IL-1 receptor, COS cells were grown and transfected as described by Cosman et al., supra, with the plasmid DNA from a 1.5 ml culture of *E. coli* transformed with pDC201 having an IL-1R cDNA insert (clone 78). After 72 hours of culture cells were harvested by washing once with 10 ml of PBS and then treating for 20 minutes at 37° C. with an EDTA solution (sodium phosphate 0.05 M, sodium chloride 0.15 M, EDTA 0.005 M, pH 7.4) followed by scraping. For comparisons, COS cells were transfected with a pDC201 control vector containing no insert, and EL-4 6.1 C10 cells and EL-4 M cells (an IL-1 receptor-negative variant of EL-4 cells) were grown and harvested as described by McDonald et al., *J. Immunol.* 135:3964, 1985.

At saturating DNA concentrations, the transfected COS cell monolayer contained an average of 45,000 sites per cell. Since the parental COS cells expressed only about 500 receptors per cell, it can be calculated that more than 98% of all IL-1 receptors in the transfected population were recombinant. Flow cytometry using FITC-IL-1α revealed that only 4.2% of the cells stained brightly; therefore, each of these transfected COS cells contained about $1.1 \times 10^6$ IL-1 binding sites.

The plasma membrane proteins of EL-4 6.1 C10 cells and of COS cells transfected with vector DNA containing cDNA encoding the IL-1 receptor (clone 78) were labeled with $^{125}$I as described in Example 1, above. Cells were subsequently extracted with PBS containing 1% Triton X-100 and a cocktail of protease inhibitors (2 mM phenylmethyl sulphonyl fluoride, 1 mM pepstatin, 1 mM leupeptin, and 2 mM O-phenanthroline). Detergent extracts were subjected to affinity chromatography as described in Example 1 on Affigel-10 (Biorad, Richmond, Calif.) to which recombinant human IL-1α had been coupled. $^{125}$I-labeled receptor was then eluted with sample buffer (0.0625 M Tris-HCl pH 6.8, 2% SDS, 10% glycerol, 5% 2-mercaptoethanol) and analyzed by SDS polyacrylamide gel electrophoresis on a 10% gel. Gels were then subjected to autoradiography. The recombinant IL-1 receptor purified by affinity chromatography in IL-1α columns migrated with a relative mobility of about 80,000 on SDS polyacrylamide gels, comparable to the mobility displayed by IL-1 receptor purified in the same manner from EL-4 6.1 C10 cells.

Figure 7A:
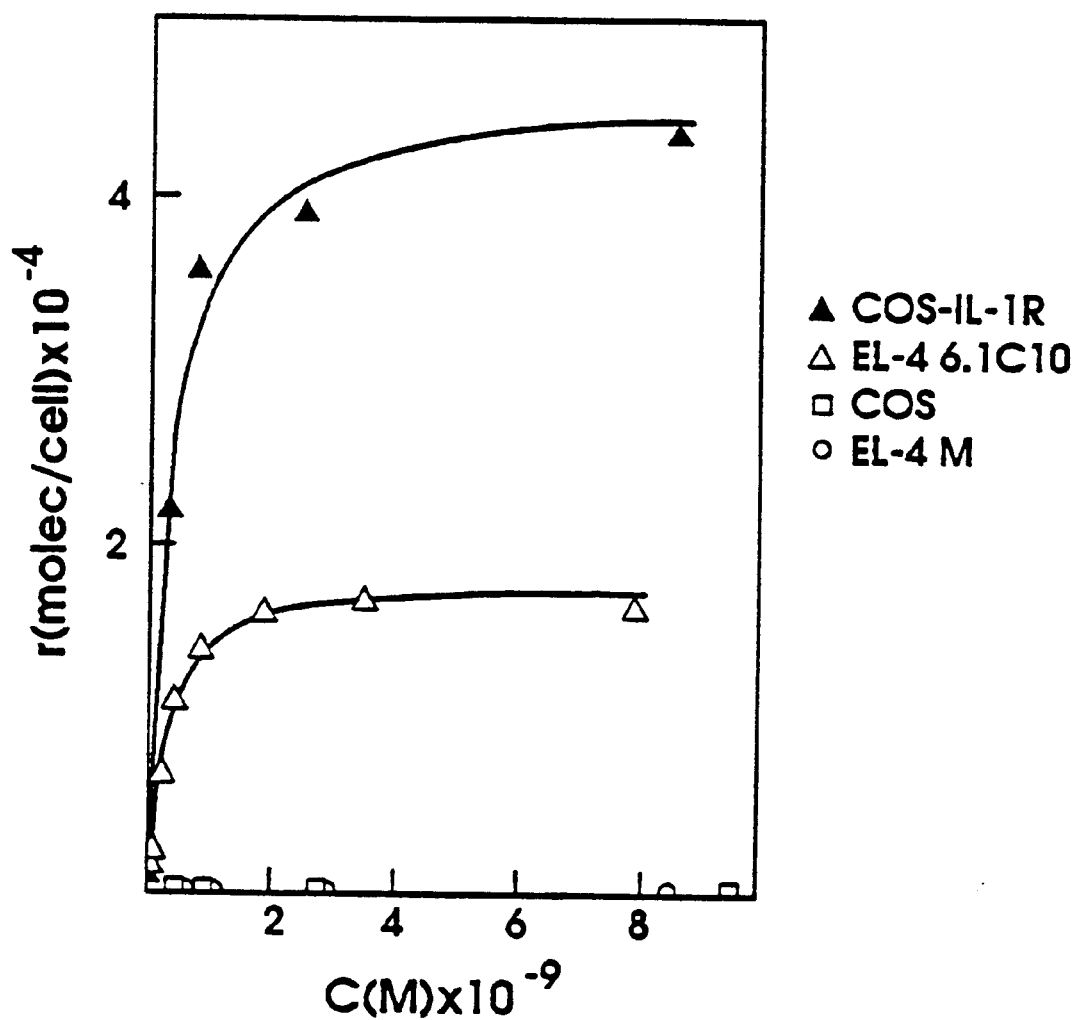
FIG. 7A compares direct binding of $^{125}$I-IL-1α to cells expression native IL-1 receptor (EL-4 6.1 C10) or recombinant receptor (CIS-IL-1R0).
Figure 7B:
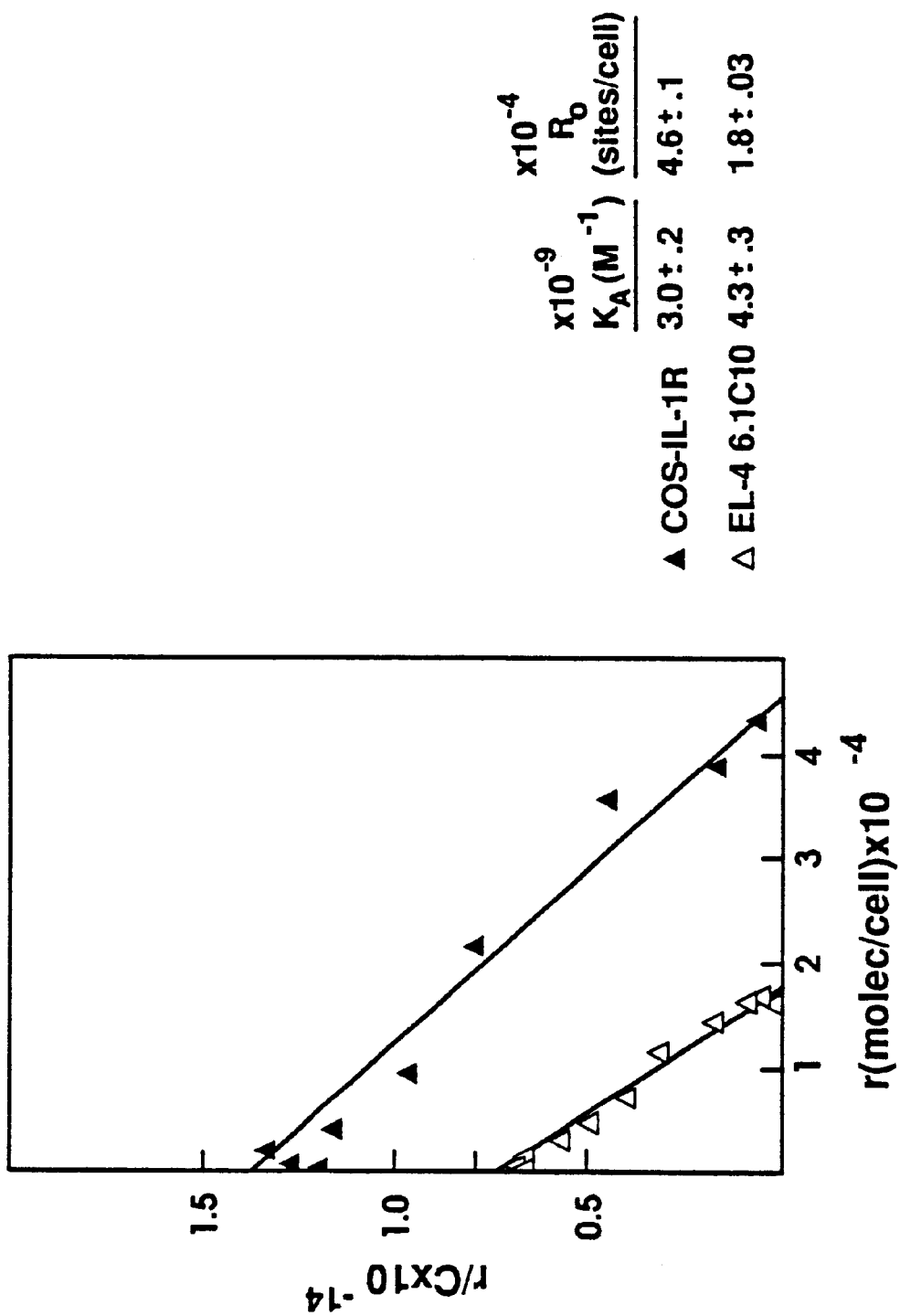
FIG. 7B shows the data from FIG. 7A) replotted in the Scatchard coordinate system.
Figure 7C:
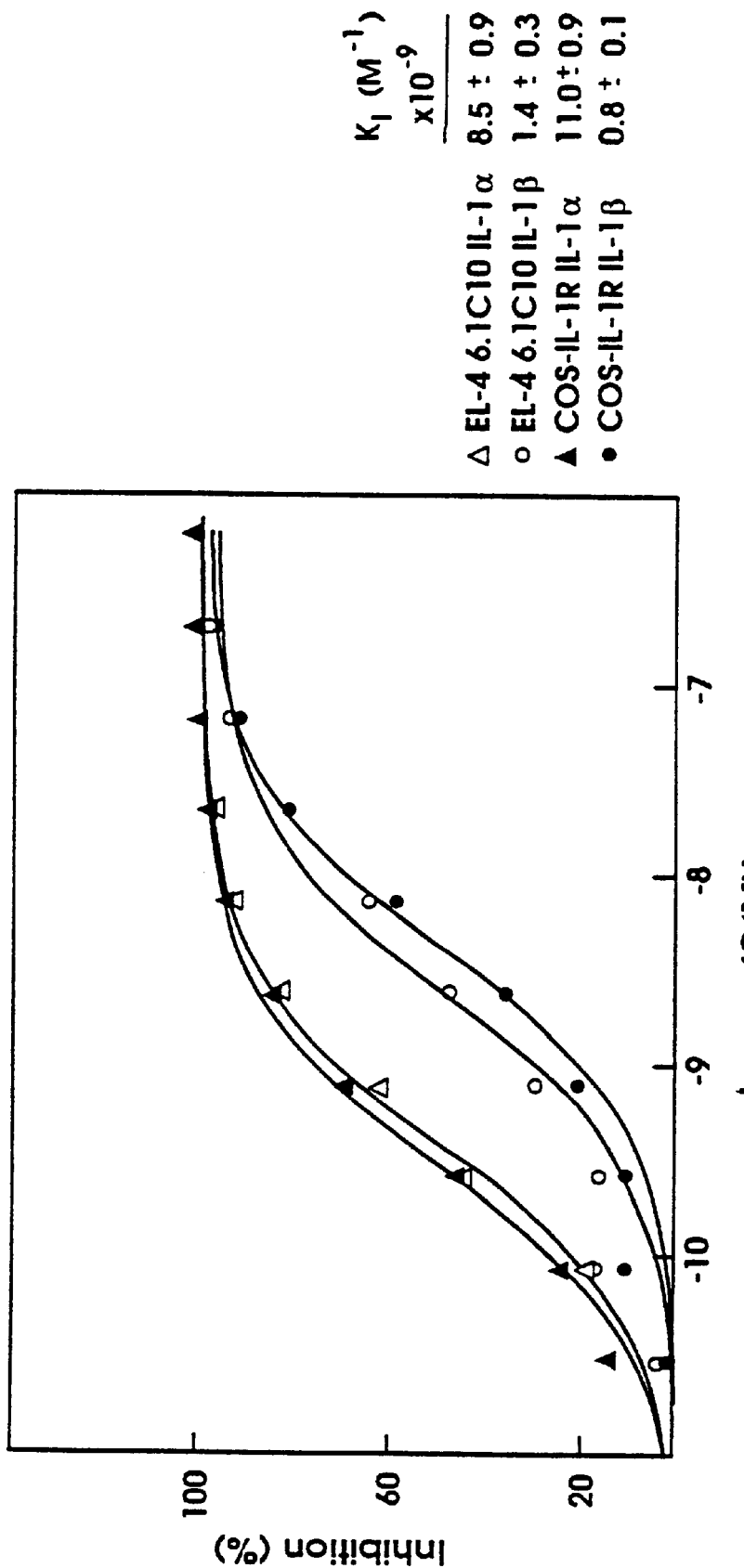
FIG. 7C indicates competition for $^{125}$I-IL-1α binding by unlabeled IL-1α and IL-1β.

The DNA from clone 78, when transfected into COS cells, led to expression of IL-1 binding activity which was virtually identical to that displayed by EL-4 6.1 C10 cells, as shown in FIGS. 7A–7C.

For binding assays, COS cells were resuspended at 1.7×$10^6$ cells/ml with ELA-4 M (1.5×$10^7$ cells/ml). All cell suspensions were made and binding assays done in RPMI 1640/10% BSA/0.1% sodium azide/20 mM HEPES pH 7.4. Binding incubations with $^{125}$I-IL-1α or $^{125}$I-IL-1β and unlabeled IL-1α and IL-1β were done as described elsewhere in the specification. $^{125}$I-IL-1α bound to the transfected COS cells with a $K_a$ of 3.0±0.2×$10^9$ $M^{-1}$ (FIG. 7B). The $K_a$ for the native receptor on EL-4 6.1 C10 cells was 4.3±3×$10^9$ $M^{-1}$. All of the binding was to recombinant receptors (see FIG. 7A); the parental COS cell population did not bind detectable $^{125}$I-IL-1α in this experiment.

In a cold competition experiment, free $^{125}$I-IL-1α concentration was 7.72±0.13 $10^{-10}$ M. On the transfected COS cells the maximal binding was 2.98±0.3×$10^4$ molecules/cell (no inhibition) and the background (measured in the presence of 6×$10^{-7}$ M unlabeled IL-1α) was 921±60 molecules/cell (100% inhibition). On the EL-4 6.1 C10 cells maximal binding was 1.33±0.02×$10^4$ molecules/cell and background (see above) was 47±2 molecules/cell. Binding of $^{125}$I-IL-1α, both to the transfected COS cells and to EL-4 6.1 C10 cells, could be competed completely by an excess of either unlabeled IL-1α or unlabeled IL-1β (FIG. 7C). The inhibition constants for IL-1α and for IL-1β were very similar with each cell type (FIG. 7C).

Example 7

Preparation of Monoclonal Antibodies to IL-1R

Preparations of purified recombinant IL-1R, for example, human IL-1R, or transfected COS cells expressing high levels of IL-1R are employed to generate monoclonal antibodies against IL-1R using conventional techniques, for example, those disclosed in the U.S. Pat. No. 4,411,993. Such antibodies are likely to be useful in interfering with IL-1 binding to IL-1 receptors, for example, in ameliorating toxic or other undesired effects of IL-1.

To immunize mice, IL-1R immunogen is emulsified in complete Freund's adjuvant an injected in amounts ranging from 10–100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay, ELISA (enzyme-linked immunosorbent assay), or inhibition of binding of $^{125}$I-IL-1α to extracts of EL-4 6.1 C10 cells (as described above). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myleoma hybrids, and spleen cell hybrids.

Hybridoma clones thus generated can be screened by ELISA for reactivity with IL-1R, for example, by adaptations of the techniques disclosed by Engvall et al., *Immunochemistry* 8:871, 1971, and in U.S. Pat. No. 4,703,004. Positive clones are then injected into the peritoneal cavities of syngeneic Balb/c mice to produce ascites containing high concentrations (>1 mg/ml) of anti-IL-1R monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

Example 8

Expression of IL-1R in Yeast

For expression of human or murine IL-1R in yeast, a yeast expression vector derived from pIXY120 is constructed as follows. pIXY120 is identical to pYαHuGM (ATCC 53157), except that it contains no cDNA insert and includes a polylinker/multiple cloning site with an NcoI site. This vector includes DNA sequences from the following sources: (1) a large SphI (nucleotide 562) to EcoRI (nucleotide 4361) fragment excised from plasmid pBR322 (ATCC 37017), including the origin of replication and the ampicillin resistance marker for selection in *E. coli;* (2) *S. cerevisiae* DNA including the TRP-1 marker, 2μ origin of replication, ADH2 promoter; and (3) DNA encoding an 85 amino acid signal peptide derived from the gene encoding the secreted peptide α-factor (see Kurjan et al., U.S. Pat. No. 4,546,082). An Asp718 restriction site was introduced at position 237 in the α-factor signal peptide to facilitate fusion to heterologous genes. This was achieved by changing the thymine residue at nucleotide 241 to a cytosine residue by oligonucleotide-directed in vitro mutagenesis as described by Craik, *Biotechniques* 3(1):12–19,1985. A synthetic oligonucleotide containing multiple cloning sites and having the following sequence was inserted from the Asp718 site at amino acid 79 near the 3' end of the α-factor signal peptide to a SpeI site in the 2μ sequence:

```
Asp718                                         StuI  NcoI  BamHI
GTACCTTTGGATAAAAGAGACTACAAGGACGACGATGACAAGAGGCCTCCATGGAT. . .
     GAAACCTATTTTCTCTGATGTTCCTGCTGCTACTGTTCTCCGGAGGTACCTA. . .
                                               |<----Polylinker--

SmaI      SpeI
    . . .CCCCCGGGACA
    . . .GGGGGCCCTGTGATC
    ---Polylinker--->|
``` pBC120 also varies from pYαHuGM by the presence of a 514 bp DNA fragment derived from the single-stranded phage f1 containing the origin of replication and intergenic region, which has been inserted at the Nru1 site in the pBR322 sequence. The presence of an f1 origin of replication permits generation of single-stranded DNA copies of the vector when transformed into appropriate strains of *E.* coli and superinfected with bacteriophage f1, which facilitates DNA sequencing of the vector and provides a basis for in vitro mutagenesis. To insert a cDNA, pIXY120 is digested with Asp718 which cleaves near the 3' end of the α-factor leader peptide (nucleotide 237) and, for example, NcoI which cleaves in the polylinker. The large vector fragment is then purified and ligated to a DNA fragment encoding the protein to be expressed.

To create a secretion vector for expressing human IL-1R, a cDNA fragment including the complete open reading frame encoding hIL-1R is cleaved with an appropriate restriction endonuclease proximal to the N-terminus of the mature protein. An oligonucleotide or oligonucleotides are then synthesized which are capable of ligation to the 5' and 3' ends of the hIL-1R fragment, regenerating any codons deleted in isolating the fragment, and also providing cohesive termini for ligation to pIXY120 to provide a coding sequence located in frame with respect to an intact α-factor leader sequence.

The resulting expression vectors are then purified and employed to transform a diploid yeast strain of *S. cerevisiae* (XV2181) by standard techniques, such as those disclosed in EPA 0165654, selecting for tryptophan prototrophs. The resulting transformants are cultured for expression of an hIL-1R protein as a secreted or extracted product. Cultures to be assayed for hIL-1R expression are grown in 20–50 ml of YPD medium (1% yeast extract, 2% peptone, 1% glucose) at 37° C. to a cell density of $1-5\times10^8$ cells/ml. To separate cells from medium, cells are removed by centrifugation and the medium filtered through a $0.45\mu$ cellulose acetate filter prior to assay. Supernatants produced by the transformed yeast strain, or extracts prepared from disrupted yeasts cells, are assayed for the presence of hIL-1R using binding assays as described above.

Example 9

Construction, Expression and Purification of Truncated Recombinant Murine IL-1 Receptor A truncated version of the IL-1 receptor protein was produced using an expression system compatible with the HELA-EBNA1 cell line, which constitutively expresses Epstein-Barr virus nuclear antigen driven from the CMV immediate-early enhancer promoter. The expression vector used was termed HAV-EO, a derivative of pDC201 which contains the Epstein-Barr virus origin and allows high level expression in the HELA-EBNA cell line. HAV-EO is derived from pDC201 by replacement of the adenovirus major late promoter with synthetic sequences from HIV-1 extending from the cap site of the viral mRNA, using the SV-40 early promoter to drive expression of the HIV-1 tat gene.

The expression construct for the soluble truncated IL-1 receptor was generated in a series of steps. The entire coding region of the receptor and part of the 5' untranslated region were removed from the original IL-1 receptor clone 78 by digestion with Asp718 and NdeI. This fragment, containing no 3' untranslated sequences, was cloned into HAV-EO, to generate HAV-EO-FL9. A variant of this plasmid, containing a translational stop codon immediately following the codon for proline 316 and lacking all the coding sequence 3' to this, was subsequently constructed by standard methods and termed HAV-EO-MEXT.

HAV-EO-MEXT vector DNA was introduced into HELA-EBNA cells by a modified polybrene transfection as disclosed by Kawai and Nishizawa (*Mol. Cell Biol.* 4:1172, 1984). $1.5\times10^6$ cells were seeded into 10 ml DMEM+10% FCS, in a 10 cm tissue culture dish. Cells were incubated at 37° C., 10% $CO_2$ for 16 hours. The media was then removed and 3 ml of serum-free DMEM containing 10 µg/ml DNA and 30 µg/ml polybrene (Sigma) were added. Dishes were then incubated at 37° C./10% $CO_2$ for a further six hours, at which time the DNA mix was removed and cells were glycerol shocked by addition of 3 ml serum-free DMEM+ 25% glycerol (v/v) for one minute. Glycerol was removed, and the cells were washed twice with medium. Ten ml of DMEM+10% FCs were then added, and the cells were incubated at 37°/10% $CO_2$ for 18 hours.

Transfected cells were then removed with trypsin and split in a ration of 1:9 into T175 $cm^2$ flasks (to give approximately 10% confluence) containing 25 ml DMEM+1% FCS. Supernatants containing transiently expressed soluble murine IL-1 receptor were harvested every 24 hours for up to ten days.

IL-1α binding activity in the medium was measured by inhibition of $^{125}$-1α to EL4 6.1 C10 cells as described by Mosley et al. (*J. Biol. Chem.* 262:2941, 1987) with the exception that labeled IL1α ($2\times10^{-11}$, 50 µl) was first incubated with the test sample (50 µl) for two hours at 8° C., prior to addition of cells ($2.5\times10^6$ cells, 50 µl). Each test sample was assayed at six dilutions (X3) and the inhibition dose response curve used to assess the relative inhibitory titer.

Soluble IL-1 receptor was purified from culture supernatants as described for natural receptor by Urdal et al. (*J. Biol. Chem.* 263:280, 1988). Culture supernatants were passed over a 1 ml bed volume IL-1α column, the column was washed with PBS and eluted with 0.1 M glycine-HCl. Acid eluate fractions were immediately neutralized and subsequently tested for IL-1 binding activity using the radioreceptor inhibition assay. SDS-polyacrylamide gel electrophoresis of the material eluted by the acid treatment showed that it contained two bands of $M_r$ 60,000 and 54,000. N-glycanase treatment of this material indicated that the size heterogeneity is due to differences in N-linked glycosylation between the two species. Soluble IL-1 receptor retains full IL-1 bonding activity.

Example 10

Generation of Monoclonal Antibodies to Murine IL-1R by Immunization with IL-1R Bearing C127 Cells Full-length murine IL-1R was prepared and inserted into C127 cells (ATTC No. CRL 1616) as described by Dower et al. in *J. Immun.* 142(12):4314–4320, 1989. Briefly, pDC201 containing the full-length IL-1R cDNA was modified by addition of the entire bovine papilloma virus genome linearized at the BamHI site. The plasmid (BX8) was then transfected into C127 cells along with the plasmid PSV2 Neo at a ratio of 10:1, and cells expressing the IL-1R were selected.

A Lewis rat was immunized intraperitoneally with $10^6$ transformed C127 cells bearing recombinant murine IL-1R three times at three-week intervals. After the animal displayed antibody titer in an inhibition assay (as described below), it was boosted intravenously with two million whole C127 cells, and three days later sacrificed.

Spleen cells were harvested from the rat and fused with NS-1 (ATCC No. T1B 18) mouse myeloma cells at a 4:1 ratio with 50% PEG MW 1500 (#807489, EM Reagents, Schuchardt, West Germany) using standard fusion procedures. Six 96 well plates were seeded with cells from each fusion at a density of 2×10⁵ total cells per well in a volume of 200 μl. Plates were fed with 100 μl of HAT media on days seven and ten and were screened on day thirteen utilizing the ELISA method, as described below in Example 15. Three clones were selected on this basis for further analysis: mIL1Rm1, m3, and m5.

Example 11

Generation of Monoclonal Antibodies to Murine IL-1R by Immunization with Soluble IL-1R A Lewis rat was immunized subcutaneously with 30 μg of purified soluble IL-1R in complete Fruend's adjuvant, followed by booster immunizations twice a week with purified soluble IL-1R in incomplete Fruend's adjuvant. After several immunizations, a sera titer of 1:1,600 (as determined by an ABC assay) had developed. A final IV boost with 5 μg of soluble IL-1R was given prior to fusion. The fusion was accomplished essentially as described above in Example 10 utilizing P3X63 Ag8.653 (ATCC No. CRL 1580) as the myeloma cell line. Fusion plates were screened by the ABC method as described below, and 5 positives were selected on this basis: mIL1Rm15, m16, m17, m18 and m19.

Example 12

Generatin of Monoclonal Antibodies to Human IL-1R by Immunization with IL-1R Bearing C127 Cells C127 cells which express human IL-1R were prepared in order to immunize animals to the IL-1R. Briefly, Gembl, a derivative of the Embl plasmid (see Dente et al., *Nucleic Acids Res.* 11:1645, 1983), was first prepared by inserting the Sp6 and T7 promoter on either side of the multiple cloning site (see, for example, pGEM-3, ProMega Biotech, Madison, Wis.). DNA encoding human IL-1R (obtained from λ9, see Sims et al., *Proc. Natl. Acad. Sci. USA* 866:8946–8950, 1989) was then inserted into the EcoRI site of Gembl, creating plasmid Gembl 9A. Gembl 9A was digested with StyI, repaired with T4 polymerase, and digested with BglII. The digestion was purified by agarose gel electrophoresis resulting in an 1863 b.p. fragment containing the sequence which encodes human IL-1R.

Trim Hixp (a derivative of pDC201, see Sims et al., *Science* 241:585, 1988, with some adenovirus sequences deleted) was next prepared in order to express human IL-1R from mammalian cells. Trim Hixp includes the following components: "SV40" contains SV40 sequences from coordinates 5171–270 including the origin of replication, enhancer sequences and early and late promoters. The fragment is oriented such that the direction of transcription is clockwise from the early promoter. The adenovirus Major Late Promoter (adMLP) contains adenovirus-2 sequences from pDC201, as discussed above, including the major late promoter, first exon and part of the intron between the first and second exons of the tripartite leader. The tripartite leader (TPL) contains the first exon and part of the intron between the first and second exons of the adenovirus-2 tripartite leader, the second exon and part of the third exon of the tripartite leader, and a multiple cloning site containing sites for Xho I, Kn I, Sma I, Not I, and Bgl I. pA contains SV40 sequences from 4127–4100 and 2770–2533 that include the polyadenylation and termination signals for early transcription. Clockwise from pA are adenovirus-2 sequences 10532–11156 containing the VAI and VAII genes, followed by pBR322 sequences from 4363–2486 and 1094–375 containing the ampicillin resistance gene and origin of replication.

Trim Hixp was digested with Pvu2 and BglIII, purified, and ligated with the Gembl 9A 1863 b.p. fragment to form HFL TXPΔTPL. HFL TXPΔTPL was digested with SfiI and XmnI, and a 3610 b.p. fragment was purified. Bx8 (which contains the full length sequence for murine IL-1R, as described above) was also digested with SfiI and XmnI to produce a 10,429 b.p. fragment, and ligated to the 3610 b.p. fragment above to form BX9AΔTPL. This plasmid was transfected into C127 cells (ATTC No. CRL 1616) as described above.

Mice were immunized intraperitoneally three times at three-week intervals with 10⁶ C127 cells bearing recombinant human IL-1R. All animals displayed inhibition of IL-1 binding titers ELISA titers to whole C127 cells. Two mice were IV boosted with two million cells and fused three days later. The mice were sacrificed and their spleen cells fused with P3X63 Ag8.653 mouse myelomas at a ratio of 4:1, with 50% PEG MW 1500 according to methods discussed above. Hybridomas were screened 10 days later by ELISA to C127 cells and positives were screened again two days later to both C127 cells and IL-1R negative PTP cells essentially as described below in Example 15. Among several clones, two were selected for further analysis: hIL1Rm1 and m10. Hybridoma hIL1Rm10 was deposited with the American Type Culture Collection Sep. 13, 1990 on 10801 University Boulevard, Manassas, Va. 20110-2209, under deposit accession number ATCC HB 10556.

Example 13

Generation of Monoclonal Antibodies to Human IL-1R by Immunization with Vaccina Bearing IL-1R cDNA containing the entire coding region of the hIL1R was inserted into the SmaI site of the vaccinia virus (VV) plasmid coexpression vector pSC11, utilizing the method essentially described by Chakrabarti et al. in *Mol. Cell Biol.* 5:3403–3409, 1985. pSC11 is available by license from the U.S. Department of Commerce, Nat'l Technical Information Service, 5285 Port Royal Road, Springfield, Va. 22161. Blue plaques were selected and used to infect either CV-1 (ATCC No. CCL 70) or HeLa (ATTC No. CCL 2) cells which were subsequently tested for expression of IL-1R. Recombinant VV from a positive plaque was then purified using conventional techniques (see Chakrabarti et al., supra; see also Elango et al., *PNAS USA* 83:1906–1910, 1986).

A Lewis rat was boosted intradermally with 10⁸ plaque forming units (pfu) of recombinant human IL-1 receptor vaccinia virus. Two weeks later the rat was boosted with 10⁶ primary rat fibroblasts infected with vaccinia virus at greater than 5 pfu per cell. Two weeks later the rat was boosted IV with 2×10⁶ C127 cells expressing recombinant human IL-1 receptor. Three days later the rat was sacrificed and its spleen cells were fused with P3X63-Ag8.653 mouse myeloma cells essentially as described above. An ELISA, as described below in Example 15, was utilized to select positive clones. One clone, hIL1Rm8, was selected for further analysis.

Example 14

Generation of Polyclonal Antibodies to Murine IL-1R by immunization with Soluble IL-1R One hundred micrograms of soluble human IL-1R was emulsified in complete Fruend's adjuvant, and administered subcutaneously to a rabbit. Booster immunizations containing 100 μg soluble IL-1R emulsified in incomplete Fruend's adjuvant were given subcutaneously every three weeks until the rabbit's antibody titer to the IL-1R had plateaued. A final booster of 100 μg soluble IL-1R was given and the rabbit was exsanguinated 9 days later.

Example 15

Assays Suitable for Detecting Antibodies

Antibodies which were prepared in Examples 10 through 14 were analyzed utilizing the assays as described below. The results of these assays are presented below in Table 1.

A. ELISA Assay

Two days prior to screening, transformed C127 and non-transformed PTP cells bearing no IL-1 receptors were seeded at a concentration of $4 \times 10^5$ cells/ml into 96-well plates to a volume of 200 μl/well. On the day of the screen, plates were washed three times with PBS and then 50 μl of hybridoma supernatants (or diluted antibody) and diluted antisera controls were added to each cell type for a 30-minute incubation at room temperature. Wells were washed three times with PBS followed by the addition of 50 μl /well of anti-species specific antisera (e.g., Goat anti-Rat Peroxidase (#172–1009) Bio-Rad) which was diluted 1:1000 in 5% fetal calf serum/PBS for 30 minutes at room temperature. Wells were washed three times with PBS and 100 μl /well of either O-Phenylenediamine(OPD) substrate solution (1 mg/ml OPD (00-2003 Zymed) and 0.001% $H_2O_2$ in 0.1 M citrate buffer pH 4.5) or TMB substrate (#507600 Kirkegaard and Perry) was added. Plates were read on a Titertek Multiscan Plate reader (#340 Flow Laboratories) after 15 minutes at either 450 nm (for OPD) or 650 nm (for TMB). Positives were selected as those wells having an absorbance with C127 cells three times greater than the corresponding signal generated with PTP cells.

B. ABC Assay 96-well, flat bottom polystyrene ELISA plates (Catalog #76-381-04, Linbro, McLean, Va.) were coated overnight with 10 μg/ml of goat anti-species specific IgG (Zymed, South San Francisco, Calif.). Plates were then blocked for 1 hour with 5% non-fat dry milk. One hundred μl of hybridoma supernatants (or diluted antibody) were then added for 1 hour. The plates were washed with PBS and 100 μl of iodinated soluble receptor was added at about 2,000 cpm/μl for 1 hour. Plates were washed and exposed to film overnight. Positive spots on the film indicate the presence of precipitated protein.

C. Modified ABC Assay 96 well flat bottom polystyrene ELISA plates ( Catalog #76-381-04, Linbro, McLean, Va.) were coated overnight with 10 μl/ml of goat anti-species specific IgG (Zymed, South San Francisco, Calif.). Plates were then blocked for 1 hour with 5% non-fat dry milk. One hundred μl of hybridoma supernatants (or diluted antibody) were then added for 1 hour. The plates were washed with PBS and 100 μl of soluble IL-1R was added for 1 hour. The plates were again washed with PBS and 2,000 cpm/μl iodinated IL1α was added for 1 hour. Plates were then washed with PBS and exposed to film overnight. Positives indicate antibodies to the IL-1 receptor that do not inhibit the binding of IL-1 to the receptor. In contrast, a negative result indicates that the antibody bound to the IL-1 binding site of the receptor, thus inhibiting or blocking the binding of the IL-1 to the receptor.

D. Cross-blocking Assay to Determine Epitopes

The relative epitopes of the isolated antibodies were determined by a cross-blocking assay to see if each antibody inhibits the binding of IL1 receptor to the other antibodies. Two μl of antibody or hybridoma supernatant was bound to a nitrocellulose sheet (#22060 Schleicher & Schuell), allowed to dry and blocked for 1 hour in 3% BSA in PBS. Supernatants were preincubated 1:1 with radioiodinated IL-1R at 2,000 cpm/μl for 1 hour. Two μl of the antibody receptor solution was then dotted over the bound antibody for 10 minutes. The nitrocellulose sheet was washed 3 times with PBS and exposed to film overnight. A diminished signal indicates that there is inhibition of one antibody's binding by another.

E. Dot Blot Immunoassay

A sheet of nitrocellulose membrane (Schleicher and Schuell, Keene, N. H.) is marked off into squares, and approximately 2 μl containing 25 ng of soluble murine or human IL-1 receptor is placed onto the membrane within each square. The IL-1R is allowed to dry, and then the sheet is blocked with 3% bovine serum albumin in PBS ("3% PBSA") for one hour. The membrane is removed from the 3% PBSA, pat dry with a towel, and 2 μl of the hybridoma supernatant or antibody is then placed directly onto the membrane. After 30 minutes the membrane is washed three times quickly with PBS, followed by two 5-minute incubations in PBS to remove excess antibody. The membrane is then incubated for 30 minutes in diluted labelled antisera which is species-specific for the antibody. For example, if the hybridoma supernatant is from a mouse monoclonal, the membrane is incubated in a 1:2000 dilution of goat anti-mouse Horse Radish Peroxidase ("HRP," Bio-Rad, Richmond, Calif). The membrane is washed as before, and color developed by incubating the membrane in a solution containing an HRP substrate (4-chloro-1-napthol) (Kirkegaard and Perry Laboratories, Gaithersburg, Md.) and hydrogen peroxide. Positives indicate the presence of antibodies which recognize the presence of the protein which was coated onto the nitrocellulose membrane.

F. Radioimmunoprecipitation (RIP)

The following were added to a 600 μl conical tube: (1) 50 μl of PBS containing 50 mg/ml bovine serum albumin and 10 μ/ml Triton X100 (New England Nuclear, Boston, Mass.) (hereinafter referred to as "PBSTA"); (2) 2 μl of rabbit anti-species specific antibody (i.e., rabbit anti mouse IgG, M, and A); (3) antibody (50 μl of hybridoma supernatant, or 2 μl of serum, or 2 μl of ascites; (4) 50 μl of 20% Protein A Sepharose solution (Protein A Sepharose CLAB, Sigma, St. Louis, Mo.); and (5) 25 μl of radioiodinated IL-1R at about 2,000 cpm/μl. The sample is spun down for two minutes at 500 rpm in a Sorvall RT6000 centrifuge. The sample is then equilibrated overnight at 4° C. on a mini-orbital shaker (Bellco, Vineland, N.J.). After incubation overnight, about 300 μl of PBS is added to each tube, and they are centrifuged for four minutes at 500 rpm. The supernatant is aspirated and the pellet is washed twice more with PBS followed by centrifugation. Radioactivity of the pellet is measured with a gamma counter. A positive indicates the presence of an immunoprecipitating antibody.

G. Inhibition Assay

C127 cells bearing IL-1 receptors were plated into 96 well plates such that on average the cells had 250,000 IL-1 receptors per cell. Briefly, the number of receptors was calculated utilizing techniques well known in the art (see Jones et al., *Molec. Immun.* 16:889, 1979). Based upon the average number of receptors on these IL-1R positive cells, non-IL-1R bearing cells (EL4) (ATCC No. TIB 39) were added such that on average cells had 250,000 IL-1 receptors per cell. $2.5 \times 10^6$ cells from this mixture were added to each well of the plate.

Antibody was added to the wells starting at 100 μg/ml followed by threefold serial dilutions. $^{125}$I-IL-1α was then added to each well, and the plate was incubated for 2 hours at 4° C. with gentle shaking. The cells and antibody were then placed into microfuge tubes containing thalate oil, and spun in a microfuge (see Jones et al., supra). This separates bound from unbound antibody. The microfuge tube was then cut in half to separate the bound antibody (pelleted cells) from the unbound antibody (remaining in suspension). The pellet was counted in a gamma counter to determine the presence of $^{125}$I. Presence of $^{125}$I indicates that the antibody does not inhibit the binding of IL1-1 to the receptor.

H. Isotyping

Isotype of monoclonals was determined utilizing either an MonoAB-ID EIA rat isotyping kit (#93-9550 Zymed), or with a Hyclone mouse isotyping kit (Logan, Utah) according to the manufacturer's instructions.

TABLE 1

Characterization of antibodies

| Antibody | ELISA | ABC | Modified ABC | Dot Blot | RIP | Inhibition | Isotype |
|---|---|---|---|---|---|---|---|
| mIL1Rm1, m3, m5 | + | + | + | weak | + | − | IgG$_{2a}$ (rat) |
| mIL1Rm15 | + | + | − | + | + | + | IgG$_{2a}$ (rat) |
| mIL1Rm16 m17, m18 | + | + | + | + | + | − | IgG$_{2a}$ (rat) |
| mIL1Rm19 | + | + | + | + | + | − | IgG$_{2b}$ (rat) |
| hIL1Rm1, m10 | + | + | − | + | + | + | IgG$_1$ (mouse) |
| hIL1Rm8, | + | + | + | + | + | − | IgG$_{2b}$ (rat) |

Example 16

Production and Purification of Antibodies

A. Production of Antibodies in Rats

Lewis rats were first primed with 0.5 ml of pristane (2,4,6,10 tramethylpentadecane, Aldrich, Milwaukee, Wis.). Two weeks later 1×10$^6$ rat bridomas (e.g., cell line mIL1Rm15) in PBS were injected intraperitoneally into the rat. Approximately two to five weeks later ascites fluid was removed from the rat, and centrifuged to remove cells and particulate matter.

B. Purification on Protein G

Two milliliters of ascites fluid was applied to a 1 ml column of protein G sepharose (Pharmacia, Piscataway, N.J.) diluted 1:1 with 0.1 M sodium acetate pH 4.5. The column was washed with 15 column volumes of sodium acetate pH 4.5. Purified antibody was then eluted with 0.1 M glycine HCl pH 3.0 and neutralized with 2 M TRIS.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A monoclonal antibody which specifically binds to a human IL-1 receptor and blocks binding of IL-1 to IL-1 receptor, wherein the human IL-1 receptor comprises the amino acid sequence of FIGS. 5A–5C.

2. A monoclonal antibody according to claim 1, selected from the group consisting of murine and human antibody.

3. A monoclonal antibody according to claim 2, wherein the murine monoclonal antibody specifically binds to a human IL-1R.

4. A monoclonal antibody according to claim 2, wherein the human monoclonal antibody specifically binds to a human IL-1 receptor.

5. A monoclonal antibody according to claim 3, wherein the murine monoclonal antibody blocks the binding of human IL-1 to human IL-1 receptor.

6. A monoclonal antibody according to claim 3, wherein the human monoclonal antibody blocks the binding of human IL-1 to human IL-1 receptor.

7. A monoclonal antibody which specifically binds to a polypeptide comprising the amino acid sequence of FIGS. 5A–5C, wherein the monoclonal antibody blocks the binding of human IL-1 to human IL-1 receptor and the monoclonal antibody is produced by the murine hybridoma ATCC HB 10556.

8. A therapeutic composition comprising a monoclonal antibody to the IL-1 receptor according to claim 1, and a physiologically acceptable carrier or diluent.

9. An antibody that binds to a polypeptide consisting of the amino acid sequence of FIGS. 5A–5C.

10. An antibody that binds to a polypeptide comprising the amino acid sequence of FIGS. 5A–5C, wherein the antibody blocks IL-1 activity.

11. An antibody of claim 9, wherein the antibody is a monoclonal antibody.

12. An antibody of claim 11, wherein the antibody is a human antibody.

13. An antibody of claim 10, wherein the antibody is a monoclonal antibody.

14. An antibody of claim 13, wherein the antibody is a human antibody.

15. An antibody of claim 13, wherein the antibody blocks the binding of human IL-1 to the polypeptide.

16. A human monoclonal antibody that specifically binds a polypeptide consisting of the amino acid sequence of FIGS. 5A–5C.

17. An antibody that binds to a polypeptide comprising the amino acid sequence of FIGS. 5A–5C wherein the antibody blocks the binding of human IL-1 to the polypeptide.

18. An antibody of claim 17, wherein the antibody is a monoclonal antibody.

19. An antibody of claim 18, wherein the antibody is a human antibody.

20. A human monoclonal antibody that binds to a polypeptide comprising the amino acid sequence of FIGS. 5A–5C wherein the antibody blocks the binding of IL-1 to the polypeptide.

21. An antibody produced by hybridoma ATCC HB 10556.

22. The hybridoma deposited in the ATCC having Accession No. HB 10556.

23. A composition comprising an antibody according to claim 1.

24. A composition comprising an antibody according to claim 2.

25. A composition comprising an antibody according to claim 3.

26. A composition comprising an antibody according to claim 12.

27. A composition comprising an antibody of claim 9.

28. A composition comprising an antibody of claim 10.

29. A composition comprising an antibody of claim 11.

30. A composition comprising an antibody of claim 18.

31. A composition comprising an antibody of claim 13.

32. A composition comprising an antibody of claim 14.

33. A composition comprising an antibody of claim 15.

34. A composition comprising an antibody of claim 16.

35. A composition comprising an antibody of claim 17.

36. A composition comprising an antibody of claim 19.

37. A composition comprising an antibody of claim 20.

38. A method for blocking the binding of IL-1 to the type I IL-1 receptor in a human, the method comprising administering to such human the antibody of claim 9.

39. A method for blocking the binding of IL-1 to the type I IL-1 receptor in a human, the method comprising administering to such human the antibody of claim 10.

40. A method for blocking the binding of IL-1to the type I IL-1 receptor in a human, the method comprising administering to such human the antibody of claim 12.

41. A method for blocking the binding of IL-1 to the type I-IL1 receptor in a human, the method comprising administering to such human the antibody of claim 17.

42. A method for blocking the binding of IL-1 to the type I IL-1 receptor in a human in need thereof, comprising administering to such human an IL-1 receptor-binding amount of a monoclonal antibody that binds the human IL-1 receptor comprising the sequence of amino acids of FIGS. 5A–5C.

* * * * *